(12) United States Patent
Miller

(10) Patent No.: US 7,326,051 B2
(45) Date of Patent: *Feb. 5, 2008

(54) METHODS AND SYSTEMS FOR TREATING TEETH

(75) Inventor: Ross Miller, Sunnyvale, CA (US)

(73) Assignee: Align Technology, Inc., Santa Clara, CA (US)

(*) Notice: Subject to any disclaimer, the term of this patent is extended or adjusted under 35 U.S.C. 154(b) by 333 days.

This patent is subject to a terminal disclaimer.

(21) Appl. No.: 10/927,169

(22) Filed: Aug. 25, 2004

(65) Prior Publication Data

US 2005/0026102 A1    Feb. 3, 2005

Related U.S. Application Data

(63) Continuation of application No. 09/751,577, filed on Dec. 29, 2000, now Pat. No. 7,074,038.

(51) Int. Cl.
*A61C 3/00* (2006.01)

(52) U.S. Cl. .............................. 433/24; 433/8

(58) Field of Classification Search ................ 433/24, 433/6, 8, 20
See application file for complete search history.

(56) References Cited

U.S. PATENT DOCUMENTS

| | | | |
|---|---|---|---|
| 2,467,432 A | 4/1949 | Kesling | |
| 3,660,900 A | 5/1972 | Andrews | |
| 3,860,803 A | 1/1975 | Levine | |
| 3,916,526 A | 11/1975 | Schudy | |
| 3,950,851 A | 4/1976 | Bergersen | |
| 4,014,096 A | 3/1977 | Dellinger | |
| 4,195,046 A | 3/1980 | Kesling | |
| 4,324,546 A | 4/1982 | Heitlinger et al. | |
| 4,348,178 A | 9/1982 | Kurz | |
| 4,478,580 A | 10/1984 | Barrut | |
| 4,504,225 A | 3/1985 | Yoshii | |
| 4,505,673 A | 3/1985 | Yoshii | |
| 4,575,805 A | 3/1986 | Moermann et al. | |
| 4,591,341 A | 5/1986 | Andrews | |
| 4,611,288 A | 9/1986 | Duret et al. | |
| 4,656,860 A | 4/1987 | Orthuber et al. | |
| 4,663,720 A | 5/1987 | Duret et al. | |

(Continued)

FOREIGN PATENT DOCUMENTS

EP    0091876 A1    10/1983

(Continued)

OTHER PUBLICATIONS

Andrews, Laurence F, "Straight Wire, the Concept and Appliances", L.A. Well Co., San Diego, Calif, 1989.*

(Continued)

*Primary Examiner*—John J Wilson
(74) *Attorney, Agent, or Firm*—Townsend and Townsend and Crew LLP

(57) ABSTRACT

A system for repositioning teeth comprises a plurality of individual appliances used with braces. The appliances are configured to be placed successively on the patient's teeth and to incrementally reposition the teeth from an initial tooth arrangement, through a plurality of intermediate tooth arrangements, and to a final tooth arrangement. The appliances may be substituted with braces as appropriate to optimize the treatment of the teeth.

33 Claims, 11 Drawing Sheets

U.S. PATENT DOCUMENTS

| | | | |
|---|---|---|---|
| 4,725,229 | A | 2/1988 | Miller |
| 4,742,464 | A | 5/1988 | Duret et al. |
| 4,755,139 | A | 7/1988 | Abbatte et al. |
| 4,763,791 | A | 8/1988 | Halverson et al. |
| 4,793,803 | A | 12/1988 | Martz |
| 4,798,534 | A | 1/1989 | Breads |
| 4,837,732 | A | 6/1989 | Brandestini et al. |
| 4,850,864 | A | 7/1989 | Diamond |
| 4,856,991 | A | 8/1989 | Breads et al. |
| 4,936,862 | A | 6/1990 | Walker et al. |
| 4,937,928 | A | 7/1990 | Van Der Zel |
| 4,964,770 | A | 10/1990 | Steinbichler et al. |
| 4,975,052 | A | 12/1990 | Spencer et al. |
| 5,011,405 | A | 4/1991 | Lemchen |
| 5,017,133 | A | 5/1991 | Miura |
| 5,027,281 | A | 6/1991 | Rekow et al. |
| 5,035,613 | A | 7/1991 | Breads et al. |
| 5,055,039 | A | 10/1991 | Abbatte et al. |
| 5,059,118 | A | 10/1991 | Breads et al. |
| 5,100,316 | A | 3/1992 | Wildman |
| 5,121,333 | A | 6/1992 | Riley et al. |
| 5,128,870 | A | 7/1992 | Erdman et al. |
| 5,131,843 | A | 7/1992 | Hilgers et al. |
| 5,131,844 | A | 7/1992 | Marinaccio et al. |
| 5,139,419 | A | 8/1992 | Andreiko et al. |
| 5,184,306 | A | 2/1993 | Erdman et al. |
| 5,186,623 | A | 2/1993 | Breads et al. |
| 5,257,203 | A | 10/1993 | Riley et al. |
| 5,273,429 | A | 12/1993 | Rekow et al. |
| 5,278,756 | A | 1/1994 | Lemchen et al. |
| 5,338,198 | A | 8/1994 | Wu et al. |
| 5,340,309 | A | 8/1994 | Robertson |
| 5,342,202 | A | 8/1994 | Deshayes |
| 5,368,478 | A | 11/1994 | Andreiko et al. |
| 5,382,164 | A | 1/1995 | Stern |
| 5,395,238 | A | 3/1995 | Andreiko et al. |
| 5,431,562 | A | 7/1995 | Andreiko et al. |
| 5,440,496 | A | 8/1995 | Andersson et al. |
| 5,447,432 | A | 9/1995 | Andreiko et al. |
| 5,452,219 | A | 9/1995 | Dehoff et al. |
| 5,454,717 | A | 10/1995 | Andreiko et al. |
| 5,456,600 | A | 10/1995 | Andreiko et al. |
| 5,474,448 | A | 12/1995 | Andreiko et al. |
| 5,518,397 | A | 5/1996 | Andreiko et al. |
| 5,533,895 | A | 7/1996 | Andreiko et al. |
| 5,542,842 | A | 8/1996 | Andreiko et al. |
| 5,549,476 | A | 8/1996 | Stern |
| 5,587,912 | A | 12/1996 | Andersson et al. |
| 5,605,459 | A | 2/1997 | Kuroda et al. |
| 5,607,305 | A | 3/1997 | Andersson et al. |
| 5,645,421 | A | 7/1997 | Slootsky |
| 5,655,653 | A | 8/1997 | Chester |
| 5,683,243 | A | 11/1997 | Andreiko et al. |
| 5,733,126 | A | 3/1998 | Andersson et al. |
| 5,740,267 | A | 4/1998 | Echerer et al. |
| 5,971,754 | A * | 10/1999 | Sondhi et al. ............... 433/24 |
| 5,975,893 | A | 11/1999 | Chishti et al. |
| 6,183,248 | B1 | 2/2001 | Chishti et al. |
| 6,217,325 | B1 | 4/2001 | Chishti et al. |
| 6,227,851 | B1 | 5/2001 | Chishti et al. |
| 6,299,440 | B1 | 10/2001 | Phan et al. |
| 6,309,215 | B1 | 10/2001 | Phan et al. |
| 6,386,864 | B1 | 5/2002 | Kuo |
| 6,398,548 | B1 | 6/2002 | Muhammad et al. |
| 6,497,574 | B1 | 12/2002 | Miller |
| 6,524,101 | B1 | 2/2003 | Phan et al. |
| 6,572,372 | B1 | 6/2003 | Phan et al. |
| 6,607,382 | B1 | 8/2003 | Kuo et al. |
| 6,705,863 | B2 | 3/2004 | Phan et al. |
| 2004/0048223 | A1 | 3/2004 | Phan et al. |

FOREIGN PATENT DOCUMENTS

| | | |
|---|---|---|
| EP | 0299490 A2 | 1/1989 |
| EP | 0376873 A2 | 7/1990 |
| EP | 0490848 A2 | 6/1992 |
| EP | 0774933 B1 | 5/1997 |
| EP | 0541500 A1 | 8/1998 |
| EP | 0731673 B1 | 9/1998 |
| FR | 2369828 | 6/1978 |
| FR | 2652256 A1 | 3/1991 |
| WO | WO 90/08512 A1 | 8/1990 |
| WO | WO 91/04713 A1 | 4/1991 |
| WO | WO 94/10935 A1 | 5/1994 |
| WO | WO 98/44865 A1 | 10/1998 |
| WO | WO 98/58596 A1 | 12/1998 |

OTHER PUBLICATIONS

Truax, "Truax Clasp-Less(TM) Appliance System", Dr. Lloyd H. Truax, The Functional Orthodontist, pp. 22-24 and 26-28, Sep./Oct. 1992.*

Alexander et al., "The DigiGraph Work Station Part 2, Clinical Manangement," *JCO* (Jul. 1990), pp. 402-407.

Altschuler et al, "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan. 1979, Special Issue A, p. 221.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler, "3D Mapping of Maxillo-Facial Prosthesis," AADR Abstract #607, 1980, 1 page total.

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A Stereophotogrammetric System for the Detection of Prosthesis Loosening in Total Hip Arthroplasty", NATO Symposium on Applications of Human Biostereometrics, Jul. 9-13, 1978, SPIE vol. 166, pp. 112-123.

Baumrind et al., Mapping the Skull in 3-D, Reprinted from The Journal, *California Dental Association*, vol. 48, No. 2 (1972 Fall Issue) 11 pages total.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. pp. 142-166.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized Diagnosis in Orthodontics for Epidemiological Studies: A Progress Report", Abstracts of Papers, *Journal of Dental Research;* vol. 67, Special Issue Mar. 9-13, 1988, p. 128.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized Analysis of Occlusion In The Postcanine Dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Biostart Operation & Training Manual, Great Lakes Orthodontics, Ltd., 199 Fire Tower Drive, Tonawanda, New York, 14150-5890, 20 pages total.
Boyd et al., "Three Dimensional Diagnosis and Orthodontic Treatment of Complex Malocclusions Wlith the Invisalign Appliance", *Seminars in Orthodontics*, vol. 7, No. 4 (Dec. 2001), p. 274-293.
Brandestini et al., "Computer Machined Ceramic Inlays: In Vitro Marginal Adaptation," *Journal of Dental Research*, vol. 64/Special Issue/Abstracts, IADR/AADR Abstracts 1985, p. 208.
Brook et al., An Image Analysis System for the Determination of Tooth Dimensions from Study Casts: Comparison with Manual Measurements of Mesio-distal Diameter, *J Dent Res.*, vol. 65, No. 3, Mar. 1986, pp. 428-431.
Burstone (interview), "Dr. Charles J. Burstone on The Uses of the Computer in Orthodontic Practice (Parts1 and 2)," *Journal of Clinical Orthodontics*, (Part 1) vol. 8, No. 7 , Jul. 1979; (Part 2) vol. 8, No. 8 pp. 539-551, Aug. 1979.
Burstone et al., "Precision Adjustment of the Transpalatal Lingual Arch: Computer Arch Form Predetermination," *Am. Journal of Orthodontics*, vol. 79, No. 2 (Feb. 1981), pp. 115-133.
Chaconas et al., "The DigiGraph Work Station, Part 1, Basic Concepts," *JCO* (Jun. 1990), pp. 360-367.
Chafetz et al., "Subsidence of the Femoral Prosthesis, A Stereophotogrammetric Evaluation," *Clinical Orthopaedics and Related Research*, No. 201 (Dec. 1985), pp. 60-67.
Chiappone, "Constructing the Gnathologic Setup And Positioner" *J. Clin. Orthod.*, 14:121-133, 1980.
Collingham, "Gnathologic Clear Plastic Positioner" *Am. J. Orthod.*, vol. 55, No. 1, ( Jan. 1969),. pp. 23-31.
Crawford, "Computers in Dentistry: Part 1: CAD/CAM: The Computer Moves Chairside," "Part 2: F. Duret—A Man With A Vision," "Part 3: The Computer Gives New Vision- Literally," "Part 4: Bytes 'N Bites" The Computer Moves From The Front Desk To The Operatory, *Canadian Dental Journal*, vol. 54(9). , (1988), pp. 661-666.
Crawford, "CAD/CAM in the Dental Office: Does It Work?" *Canadian Dental Journal*, vol. 57, No. 2 (Feb. 1991), pp. 121-123.
Crooks, "CAD/CAM Comes to USC," *USC Dentistry*, (Spring 1990) pp. 14-17.
Cureton, "Correcting Malaligned Mandibular Incisors With Removable Retainers" *J. Clin. Orthod.*, 30:390-395, 1996.
Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.
Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.
DCS Dental AG, "The CAD/CAM 'DCS Titan System' for Production of Crowns/Bridges" *DSC Production AG*, Jan. 1992, pp. 1-7.
Defranco et al., "Three-Dimensional Large Displacement Analysis of Orthodontic Appliances," *J. Biomechanics*, vol. 9 (1976), pp. 793-801.
Dental Institute University of Zurich Switzerland, Program for International Symposium on Computer Restorations: State of the Art of the CEREC-Method, May 1991, 2 pages total.
DenTrac Corporation, Dentrac document, pp. 4-13.
Duret et al, "CAD-CAM in Dentistry," *Journal of the American Dental Association*, vol. 117 (Nov. 1988), pp. 715-720.
Duret et al., "CAD/CAM Imaging in Dentistry," *Current Opinion in Dentistry*, vol. 1 (1991), pp. 150-154.
Duret, "Vers une prosthese informatisee," (English translation also attached), *Tonus*, vol. 75, (Nov. 15, 1985), pp. 55-57.
Duret, "The Dental CAD/CAM, General Description of the Project," *Hennson International Product Brochure*, Jan. 1986., 18 pages total.
Economides, "The Microcomputer in the Orthodontic Office," *JCO*, (Nov. 1979), pp. 767-772.
Elsasser, "Some Observations on the History and Uses of the Kesling Positioner" *Am. J. Orthod.*, vol. 36, No. 5, (May 1950) pp. 368-374.

Faber et al., "Computerized interactive orthodontic treatment planning," *Am. J. Orthod.*, vol. 73, No. 1 (Jan. 1978), pp. 36-46.
Felton et al. "A computerized analysis of the shape and stability of mandibular arch form," *Am. Journal of Orthodontics and Dentofacial Orthopedics*, vol. 92, No. 6 (Dec. 1987), pp. 478-483.
Friede et al., "Accuracy of Cephalometric Prediction in Orthognathic Surgery," Abstract of Papers, *Journal of Dental Research*, vol. 70 (1987), pp. 754-760.
Gim-Alldent Deutschland, "Das DUX System: Die Technik" 2 pages total.
Grayson, "New Methods for Three Dimensional Analysis of Craniofacial Deformity," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5-6.
Guess et al., "Computer Treatment Estimates in Orthodontics and Orthognathic Surgery," *JCO*, (Apr. 1989), pp. 262-28.
Heaven et al., "Computer-based Image Analysis of Artificial Root Surface Caries," Abstracts of Papers, *Journal of Dental Research*, vol. 70,Apr. 17-21, 1991, p. 528.
Hoffmann et al., "Role of Cephalometry for Planning of Jaw Orthopedics and Jaw Surgery Procedures," (Article Summary in English, article in German), *Informationen*, (Mar. 1991), pp. 375-396.
Huckins, "CAD-CAM Generated Mandibular Model Prototype from MRI Data," *AAOMS* 1999, p. 96.
JCO Interviews, "Craig Andreiko , DDS, MS on the Elan and Orthos Systems", JCO, (Aug. 1994), pp. 459-468.
JCO Interviews, "Dr. Homer W. Phillips on Computers in Orthodontic Practice, Part 2" JCO, (Dec. 1983), pp. 819-831.
Jerrold, "The Problem, Electronic Data Transmission and the Law," *AJO-DO*, (Apr. 1988), pp. 478-479.
Jones et al., "An Assessment of the Fit of a Parabolic Curve to Pre- and Post-Treatment Dental Arches," *British Journal of Orthodontics*, vol. 16 (1989), pp. 85-93.
Kamada et al., "Case Reports on Tooth Positioners Using LTV Vinyl Silicone Rubber" J. Nihon University School of Dentistry, 26(1):11-29, 1984.
Kamada et al., "Construction of Tooth Positioners With LTV Vinyl Silicone Rubber and Some Case Reports" J. Nihon University School of Dentistry, 24(1):1-27, 1982.
Kanazawa et al., "Three-Dimensional Measurements of the Occlusal Surfaces of Upper Molars in a Dutch Population," *J. Dent Res.* , vol. 63, No. 11 (Nov. 1984), pp. 1298-1301.
Kesling, "Coordinating the Predetermined Pattern and Tooth Positioner With Conventional Treatment" *Am. J. Orthod. Oral. Surg.*, 32:285-293, 1946.
Kesling, "The Philosophy of the Tooth Positioning Appliance" *Am. J. Orthod. Oral. Surg.*, 31(6):297-304, 1945.
Kleemann et al., "The Speed Positioner" *J. Clin. Orthod.*, 30:673-680, 1996.
Kuroda et al., "Three-dimensional dental cast analyzing system using laser scanning" *Am. J. Orthod. Dentofac. Orthop.*, 110:365-369, 1996.
Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.
Leinfelder et al., "A new method for generating ceramic restorations: a CAD-CAM system," *Journal Of The American Dental Assoc.*, vol. 118, No. 6 (Jun. 1989), pp. 703-707.
Manetti et al., "Computer-aided Cefalometry and New Mechanics in Orthodontics" (Article Summary in English, article in German), *Fortschr. Kierferorthop.* 44, 370-376 (Nr. 5), 1983.
McCann, Inside the ADA, *Journal Of The American Dental Assoc.*, vol. 118 (Mar. 1989) pp. 286-294.
McNamara et al., "Invisible Retainers", *J. Clinical Orthodontics*, (Aug. 1985) pp. 570-578.
McNamara et al., Chapter 19: Invisible Retainers, *Orthodontic and Orthopedic Treatment in the Mixed Dentition*, Needham Press, Jan. 1993, pp. 347-353.

Moermann et al., "Computer Machined Adhesive Porcelain Inlays: Margin Adaptation after Fatigue Stress," IADR Abstract 339, *Journal of Dental Research*, vol 66(a) (1987), p. 763.

Mörmann et al., "Marginal Adaptation von adhasiven Porzellaninlays in vitro," *Schwizerische Monatsshrift fur Zahnmedizin*, vol. 85 (1985), p. 1118-1129.

Nahoum, "The Vacuum Formed Dental Contour Appliance" *The New York State Dental Journal*, 30(9):385-390, Nov. 1964.

Nash, "CEREC CAD/CAM Inlays: Aesthetics and Durability in a Single Appointment," *Dentistry Today*, (Oct. 1990), pp. 20, 22-23, 54.

*Nippon Dental Review* "New orthodontic device-dynamic positioner (.D.P.)-I. Approach to the proposal of D.P. and transparent silicone rubber" (1980) 452:61-74.

*Nippon Dental Review* "New orthodontic device-dynamic positioner (D.P.)-II. Practical application and construction of D.P." (1980) 454:107-130.

*Nippon Dental Review* "New orthodontic device-dynamic positioner (D.P.)-III. Case reports of reversed occlusion" (1980) 457:146-164.

*Nippon Dental Review* "New orthodontic device-dynamic positioner (D.P.)-Case reports of reversed occlusion" (1980) 458:112-129.

Nishiyama et al., "A New Construction Of Tooth Repositioner By LTV Vinyl Silicone Rubber" J. Nihon University School of Dentistry, 19(2):93-102, 1977.

Pinkham, "'Foolish' Concept Propels Technology," *Dentist*, Jan./Feb. 1989, 3 pages total.

Pinkham, "Inventor's CAD/CAM May Transform Dentistry," *Dentist*, Sep. 1990, 3 pages total.

Ponitz, "Invisible Retainers", *Am. J. Orthodontics*, vol. 59, No. 3, Mar. 1971, pp. 266-272.

Procera Research Projects, *PROCERA Research Projects 1993—Abstract Collection*, 1993, pp. 3-24.

*Raintree Essix™ & ARS Materials, Inc.*, Raintree Essix™ Technical Magazine Table of Contents and Essix™ Applications, http://www.essix.com/magazine/default.html (Aug. 13, 1997) 7 pages total.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, "Feasibility of an Automated System for Production of Dental Restorations," PhD Thesis, Univ. of Minnesota, Nov. 1988, 244 pages total.

Richmond et al., Research Reports, "The Development of a 3D Cast Analysis System," *British Journal of Orthodontics*, vol. 13, No. 1, (Jan. 1986) pp. 53-54.

Richmond, "Recording The Dental Cast In Three Dimensions," *Am. J. Orthod. Dentofac. Orthop.*, vol. 92, No. 3, (Sep. 1987), pp. 199-206.

Rudge, "Dental arch analysis: Arch Form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computed Tomography in Maxillofacial Surgical Planning," *Arch Otolarngol Head Neck Surg.* vol. 114 (Apr. 1988), pp. 438-442.

Shilliday, "Minimizing Finishing Problems With the Mini-Positioner" *Am. J. Orthod.* 59:596-599, 1971.

Siemens, "CEREC—Computer-Reconstruction," High Tech in der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), *Dtsch Zahnärztl Z 45*, 314-322, 1990.

U.S. Department of Commerce, National Technical Information Service, "Automated Crown Replication Using Solid Photography SM," Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

U.S. Appl. No. 60/199,485; filed Apr. 25, 2000; 23 pages total.

U.S. Appl. No. 60/235,240; filed Sep. 25, 2000; 21 pages total.

Van Der Linden et al., "Three-Dimensional Analysis of Dental Casts by Means of the Optocom," *J Dent Res*, Jul.-Aug. 1972, vol. 51, No. 4, p. 1101.

Van Der Linden, "A New Method to Determine Tooth Positions and Dental Arch Dimensions," Jul.-Aug. 1972, p. 1104.

Van Der Zel, "Ceramic-fused-to-metal Restorations with a New CAD/CAM System," *Quintessence International*, vol. 24(11) (1993), pp. 769-778.

Várady et al., Reverse Engineering Of Geometric Models—An Introduction. Computer-Aided Design, 29 (4):255-268, 1997.

Warunek et al., "Clinical Use Of Silicone Elastomer Appliances" *JCO*, MH (10):694-700, 1989.

Warunek et al., "Physical And Mechanical Properties of Elastomers in Orthodontic Positioners" *Am. J. Orthod. Dentofac. Orthop.*, 95:388-400, 1989.

Wells, "Application of the Positioner Appliance in Orthodontic Treatment" *Am. J. Orthodont.*, 58:351-366, 1970.

Williams, "Dentistry and CAD/CAM: Another French Revolution," *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical Measurement of Dental Cast Profile and Application to Analysis of Three-Dimensional Tooth Movement in Orthodontics," *Frontiers in Med. and Biol. Eng'g*, vol. 1, No. 2 (1988), pp. 119-130.

\* cited by examiner

METHODS AND SYSTEMS FOR TREATING TEETH

CROSS-REFERENCES TO RELATED APPLICATIONS

The present application is a continuation of and claims the benefit of priority; from U.S. patent application Ser. No. 09/751,577, filed on Dec. 29, 2000, now U.S. Pat. No. 7,074,038 the full disclosure of which is incorporated herein by reference. The full disclosure of U.S. patent application Ser. No. 09/466,353, filed on Dec. 17, 1999, and now U.S. Pat. No. 6,398,548, is also incorporated herein by reference.

BACKGROUND OF THE INVENTION

1. Field of the Invention

The present invention is related generally to the field of orthodontics. More particularly, the present invention is related to a method and system for repositioning teeth from an initial tooth arrangement to a final tooth arrangement.

2. Description of the Background Art

Tooth positioners for finishing orthodontic treatment are described by Kesling in the *Am. J. Orthod. Oral. Surg.* 31:297-304 (1945) and 32:285-293 (1946). The use of silicone positioners for the comprehensive orthodontic realignment of a patient's teeth is described in Warunek et al. (1989) *J. Clin. Orthod.* 23:694-700. Clear plastic retainers for finishing and maintaining tooth positions are commercially available from Raintree Essix, Inc., New Orleans, La. 70125, and Tru-Tain Plastics, Rochester, Minn. 55902. The manufacture of orthodontic positioners is described in U.S. Pat. Nos. 5,186,623; 5,059,118; 5,055,039; 5,035,613; 4,856,991; 4,798,534; and 4,755,139. The use of two or more vacuum-formed appliances for effecting orthodontic treatment is suggested in Nahoum (1964) *N.Y. State D.J.* 30:385-390.

Other publications describing the fabrication and use of dental positioners include Kleemann and Janssen (1996) *J. Clin. Orthodon.* 30:673-680; Cureton (1996) *J. Clin. Orthodon.* 30:390-395; Chiappone (1980) *J. Glin. Orthodon.* 14:121-133; Shilliday (1971) *Am. J. Orthodontics* 59:596-599; Wells (1970) *Am. J. Orthodontics* 58:351-366; and Cottingham (1969) *Am. J. Orthodontics* 55:23-31.

Kuroda et al. (1996) *Am. J. Orthodontics* 110:365-369 describes a method for laser scanning a plaster dental cast to produce a digital image of the cast. See also U.S. Pat. No. 5,605,459.

U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the jaw is described in U.S. Pat. Nos. 5,342,202 and 5,340,309. Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

Recently, a new system for treating dental malocculsions has become available under the trade name Invisalign™ System. The Invisalign™ System has two components. The first component is called ClinCheck® and allows practitioners to simulate treatment of teeth by observing and modeling two-week stages of tooth movement. Based on the results of the ClinCheck® component, the second component comprises aligners which are thin, clear, plastic removable dental appliances that correspond to each treatment stage of the ClinCheck® simulation. The aligners are manufactured using advanced computer-controlled fabrication systems. Each aligner is worn by the patient for approximately two weeks before it is exchanged for a next stage aligner intended to further reposition the teeth. The Invisalign™ System addresses many of the significant limitations of conventional braces. In particular, the Invisalign™ System aligners are virtually invisible, and are therefore more aesthetically pleasing for the patient. Second, the aligners are generally less painful and uncomfortable than are traditional braces. Additionally, the aligners can be removed to permit conventional oral hygiene, thus being more healthy for the patient's teeth.

A present shortcoming of the Invisalign™ System, however, is that not all malocculsions can be effectively treated using the removable aligners. Certain tooth repositioning steps, such as extrusion, certain rotations, and the like, can be difficult to achieve with the present Invisalign™ System. For those reasons, it would be desirable to provide improved methods and systems for treating dental malocculsions which at least partially retain the benefits and advantages of the removable aligners of the Invisalign™ System.

Information concerning the Invisalign™ System can be found at the website of Align Technology, Inc. (www.invisalign.com). The Invisalign™ System is described in U.S. Pat. No. 5,975,893, the full disclosure of which is incorporated herein by reference. Other aspects of and potential improvements of the Invisalign™ System are described in the following published PCT applications and pending U.S. patent applications, the full disclosures of which are incorporated herein by reference. They are as follows: Method and system for incrementally moving teeth, filed Apr. 23, 1999, Ser. No. 09/298,268, and now U.S. Pat. No. 6,217,325; System and method for releasing tooth positioning appliances, filed Feb. 16, 1999, Ser. No. 09/250,962, and now U.S. Pat. No. 6,183,248; Composite articles and methods for destructive scanning, filed Sep. 25, 2000, Ser. No. 60/235,240; Manipulable dental model system for fabrication of a dental appliance, filed Dec. 3, 1999, Ser. No. 09/454,786, and now U.S. Pat. No. 6,227,851; Attachment devices and methods for a dental appliance, filed Dec. 3, 1999, Ser. No. 09/454,278, and now U.S. Pat. No. 6,309,215; System and method for producing tooth movement, filed Jan. 14, 2000, Ser. No. 09/483,071, and now U.S. Pat. No. 6,299,440; Systems and methods for varying elastic modulus appliances, filed Jul. 14, 2000, Ser. No. 09/616,830, and now U.S. Pat. No. 6,524,101; Embedded features and methods of a dental appliance, filed Jul. 14, 2000, Ser. No. 09/616,222, and now U.S. Pat. No. 6,572,372; Methods and systems for modeling bite registration, filed Apr. 25, 2000, Ser. No. 60/199,485; Modified tooth positioning appliances and methods and systems, filed Sep. 8, 2000, Ser. No. 09/658,340, and now U.S. Pat. No. 6,497,574; Stress indicators for tooth positioning appliances, filed Jun. 30, 2000, Ser. No. 09/608,593, and now U.S. Pat. No. 6,386,864; and Methods and systems for concurrent tooth repositioning and substance delivery, filed Sep. 21, 2000, Ser. No. 09/666,783, and now U.S. Pat. No. 6,607,382.

BRIEF SUMMARY OF THE INVENTION

The present invention provides improved methods and systems for repositioning teeth from an initial tooth arrangement to a final tooth arrangement. The system for repositioning teeth comprises both polymeric shell appliances and one or more wire and bracket appliance(s). The polymeric shell appliances are configured to be placed successively on the patient's teeth and to incrementally reposition the teeth from a beginning tooth arrangement (which may or may not be the initial tooth arrangement), through a plurality of intermediate tooth arrangements, and to a final tooth arrangement. The polymeric shell appliances will be used in combination with conventional wire and bracket "braces" as appropriate to effect full treatment of the teeth. The polymeric shell appliances, which may be aligners from the Invisalign™ System, may be used either before or after the wire and bracket appliance(s). Moreover, in some cases, it may be beneficial to intersperse treatment of the patient with aligners for a period of time, with wire and bracket appliance(s) for a period of time, and then to repeat either or both of the polymeric shell appliance treatment and the wire and bracket appliance treatment. The particular order and/or repetition of treatment modalities may be selected depending on the particular patient requirements.

Repositioning is accomplished with a system comprising a series of polymeric shell appliances configured to receive the teeth in a cavity and incrementally position the individual teeth in a series of successive steps. The polymeric shell appliances are used in connection with braces to effect a full course of tooth movement. The polymeric shell appliances each have a geometry selected to reposition the teeth from one arrangement to a subsequent arrangement. The appliances comprise polymeric shells having cavities and the cavities of successive shells have different geometries shaped to receive and resiliently reposition teeth from the first to the second arrangement. One or more wire and bracket systems, usually referred to as "braces," also reposition the teeth from one arrangement to a successive arrangement, the brackets and appliances being deployed in a preselected order to reposition teeth from the initial tooth arrangement to the final tooth arrangement. Most often, the wire and bracket appliance(s) will be employed first in order to partially reposition the teeth to bring the patient within certain guidelines regarding the appropriate use of the polymeric shell appliances. In other instances, it may be desirable to employ the polymeric shell appliances first in order to achieve certain treatment goals prior to finishing or further treatment with a wire and bracket appliance. The tooth positions defined by the cavities in each successive polymeric shell appliance differ from those defined by the prior appliance by no more than 2 mm, usually less than 1 mm, and typically less than 0.5 mm. The system will include at least three polymeric appliances, usually at least ten polymeric appliances, although complex cases involving many of the patient's teeth may take twenty-five or more polymeric appliances.

An optional aspect of the present invention will be to provide criteria which enable the practitioner to distinguish between a less severe malocclusion and a more severe malocclusion. Generally, less severe malocculsions will be those in which it is expected that the patient may be treated only with the polymeric shell appliances in order to achieve a desired teeth reconfiguration. In contrast, patients who have a more severe malocclusion (as determined in accordance with the criteria), will usually require a combination treatment using both polymeric shell appliances during one or more portions of the treatment and wire and bracket appliance(s) during one or more other portions of the treatment. Exemplary criteria are as follows.

a) A-P correction of greater than 2 mm;
    b) Autorotation of the mandible required for vertical/A-P correction;
    c) CR-CO discrepancy correction/treatment to other than centric occlusion;
    d) Correction of moderate to severe rotations of premolars and/or cannines that are greater than 20 degrees;
    e) Severe deep bite opened to ideal or open bite to be closed to ideal;
    f) Extrusion of teeth greater than 1 mm other than as part of torquing or in conjunction with intrading adjacent teeth;
    g) Teeth tipped by more than 45 degrees;
    h) Multiple missing teeth;
    i) Crowns less than 70% of normal size;
    j) Posterior open bite; and
    k) Movement of entire arch required for A-P correction.

Patients who meet none of the above criteria will usually be considered to have malocclusions which can be treated using polymeric shell appliances without the need to employ wire and bracket appliance(s) at any point during treatment. In many instances, patients who have only one or two of the listed criteria may also be successfully treated using polymeric shell appliances alone. The decision may be based on the treating professional's judgment, with patient consent, and may be based on the particular patient's condition and prognosis.

According to a method of the present invention, a patient's teeth are repositioned from an initial tooth arrangement to a final tooth arrangement by successively placing one or more appliances having geometries selected to progressively reposition the teeth from a first arrangement to successive arrangements. The current appliance can be replaced with a new appliance or with one or more brackets to progressively reposition the teeth, the brackets and appliances being deployed in seriatim to reposition teeth from the initial tooth arrangement to the final tooth arrangement. The tooth positions defined by the cavities in each successive appliance differ from those defined by the prior appliance by no more than 2 mm. The successive placing step may include placing at least two to ten or possibly up to twenty-five additional appliances. The appliances are successively replaced at an interval in the range from two days to twenty days.

An improved method for repositioning teeth using appliances comprises polymeric shells having cavities shaped to receive and resiliently reposition teeth to produce a final tooth arrangement, wherein the improvement comprises determining at the outset of treatment geometries for at least three appliances. The appliances are to be worn successively by a patient to reposition teeth from an initial tooth arrangement to the final tooth arrangement, wherein the cavities of successive shells have different geometries with at least four geometries with the potential for at least ten to twenty-five geometries determined at the outset. The tooth positions defined by the cavities in each successive appliance differ from those defined by the prior appliance by no more than 2 mm. In lieu of a successive appliance, one or more braces can be used to move teeth.

As will be described in more detail below in connection with the methods of the present invention, the systems may be planned and all individual appliances fabricated at the outset of treatment, and the appliances may thus be provided to the patient as a single package or system. The order in which the appliances are to be used will be clearly marked, (e.g., by sequential numbering) so that the patient can place the appliances over his or her teeth at a frequency prescribed by the orthodontist or other treating professional. Unlike braces, the patient need not visit the treating professional every time an adjustment in the treatment is made. While the patients will usually want to visit their treating professionals periodically to assure that treatment is going according to the original plan, eliminating the need to visit the treating professional each time an adjustment is to be made allows the treatment to be carried out in many more, but smaller, successive steps while still reducing the time spent by the treating professional with the individual patient. Moreover, the ability to use polymeric shell appliances that are more comfortable, less visible, and removable by the patient, greatly improves patient compliance, comfort, and satisfaction.

In general, the transition to the next appliance or brace adjustment can be based on a number of factors. Most simply, the appliances can be replaced on a predetermined schedule or at a fixed time interval (i.e. number of days for each appliance) determined at the outset based on an expected or typical patient response. Alternatively, actual patient response can be taken into account, e.g., a patient can advance to the next appliance when that patient no longer perceives pressure on their teeth from a current appliance, i.e. the appliance they have been wearing fits easily over the patient's teeth and the patient experiences little or no pressure or discomfort on his or her teeth. In some cases, for patients whose teeth are responding very quickly, it may be possible for a treating professional to decide to skip one or more intermediate appliances, i.e. reduce the total number of appliances being used below the number determined at the outset. In this way, the overall treatment time for a particular patient can be reduced. In other situations, for patients whose teeth do not respond as planned, braces may be used to reposition teeth.

In a particular aspect of the present invention, an improved method for repositioning teeth utilizes both polymeric shell appliances having cavities shaped to receive and resiliently reposition teeth and wire and bracket systems which are used sequentially with the polymeric shell appliances. Preferably, the wire and bracket system will be used initially to reposition the teeth prior to applying the polymeric shell appliances. For example, the wire and bracket system can be used to bring the patient to a tooth configuration within the criteria set forth above. After the teeth are brought into within the criteria, the polymeric shell appliances can be used to achieve a final tooth arrangement, typically utilizing at least four appliances, more usually at least ten appliances, and often at least twenty-five appliances.

In a further aspect of the present invention, methods for treating a dental malocclusion comprise providing criteria to distinguish between a less severe malocclusion and a more severe malocclusion. Exemplary criteria have been set forth above. Whether an individual patient's malocclusion is more or less severe is determined in accordance with the criteria. Usually, patients who are free from all of the individual criteria set forth above will be considered to have a less severe malocclusion, thereby indicating treatment with a plurality of successive polymeric shell appliances typically without any use of a wire and bracket system. If, on the other hand, the malocclusion is determined to be more severe, the indicated treatment will include both the use of the polymeric shell appliances as well as the use of a wire and bracket system. The treatment may occur in either order, with either the polymeric shell appliances, or the wire and bracket system being used first. The combined treatment, in either case, will be sufficient to reposition the teeth to a final desired arrangement.

A list may be provided in a variety of ways. Most commonly, the list will be provided in written form, optionally as part of a "check list" which is filled out by the treating practitioner prior to commencing treatment. The use of a check list helps assure compliance and permits review by others. In other cases, the list may be provided electronically, e.g., over the web or on software provided to individual practitioners. The use of an electronic list, particularly over the web, is useful since it permits updating of the criteria as additional information is learned regarding treatment protocols.

Whether or not the malocclusion is more or less severe can be determined in a variety of ways. Alternatively, determining whether the malocclusion is more or less severe may comprise obtaining a physical or digital model of the patient's teeth, thus permitting remote consideration of the malocclusion. That is, the physical or digital model can be transported to a central location for examination and evaluation. Physical models will typically be a casting taken directly from the patient's teeth. Digital models may be obtained from such castings or alternatively may be obtained directly using intra-oral scanning techniques, such as those described in U.S. Pat. No. 4,935,635, the full disclosure of which is incorporated herein by reference.

DETAILED DESCRIPTION OF THE INVENTION

According to the present invention, systems and methods are provided for incrementally moving teeth using a plurality of discrete appliances, where each appliance successively moves one or more of the patient's teeth by relatively small amounts. The tooth movements will be those normally associated with orthodontic treatment, including translation in all three orthogonal directions relative to a vertical centerline, rotation of the tooth centerline in the two orthodontic directions ("root angulation" and "torque"), as well as rotation about the centerline.

Figure 1A:
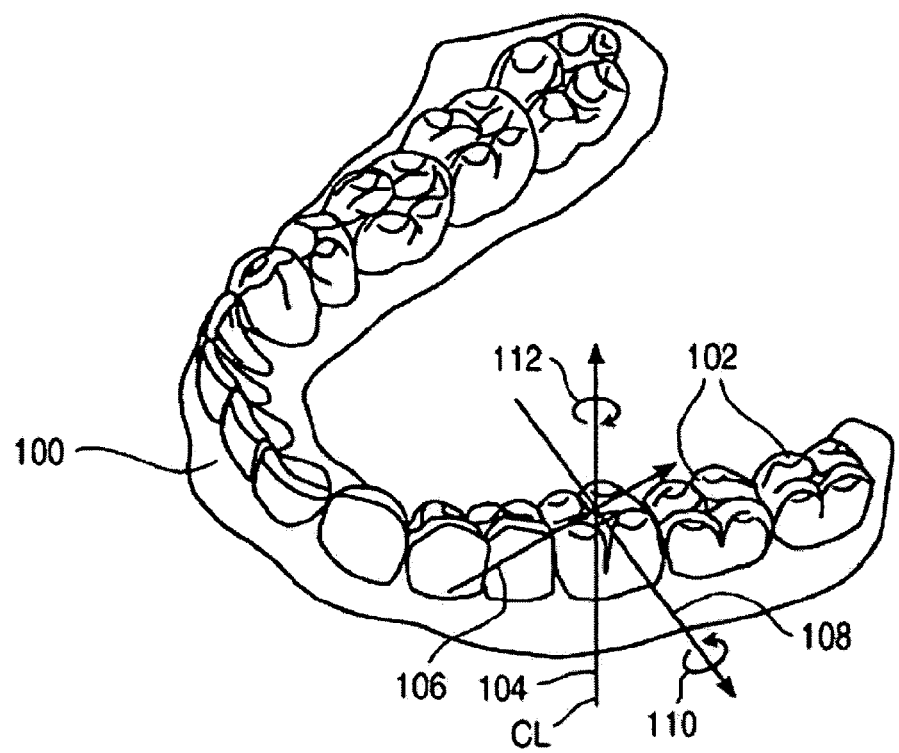
FIG. 1A illustrates a patient's jaw and provides a general indication of how teeth may be moved by the methods and apparatus of the present invention.
Figure 1B:
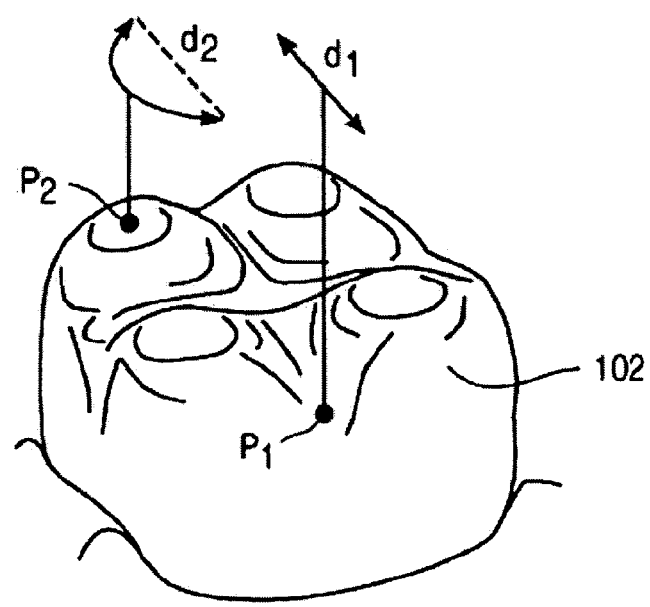
FIG. 1B illustrates a single tooth from FIG. 1A and defines how tooth movement distances are determined.

Referring now to FIG. 1A, a representative jaw 100 includes a plurality of teeth 102. The present invention is intended to move at least some of these teeth from an initial tooth arrangement to a final tooth arrangement. To understand how the teeth may be moved, an arbitrary centerline (CL) is drawn through one of the teeth 102. With reference to this centerline (CL), the teeth may be moved in the orthogonal directions represented by axes 104, 106, and 108 (where 104 is the centerline). The centerline may be rotated about the axis 108 (root angulation) and 104 (torque) as indicated by arrows 110 and 112, respectively. Additionally, the tooth may be rotated about the centerline. Thus, all possible free-form motions of the tooth can be performed. Referring now to FIG. 1B, the magnitude of any tooth movement achieved by the methods and devices of the present invention will be defined in terms of the maximum linear translation of any point P on a tooth 102. Each point $P_i$ will undergo a cumulative translation as that tooth is moved in any of the orthogonal or rotational directions defined in FIG. 1A. That is, while the point will usually follow a non-linear path, there will be a linear distance between any point in the tooth when determined at any two times during the treatment. Thus, an arbitrary point $P_1$ may in fact undergo a true side-to-side translation as indicated by arrow $d_1$, while a second arbitrary point $P_2$ may travel along an arcuate path, resulting in a final translation $d_2$. Many aspects of the present invention are defined in terms of the maximum permissible movement of a point $P_i$ induced by the methods in any particular tooth. Such maximum tooth movement, in turn, is defined as the maximum linear translation of that point $P_i$ on the tooth which undergoes the maximum movement for that tooth in any treatment step.

Figure 1C:
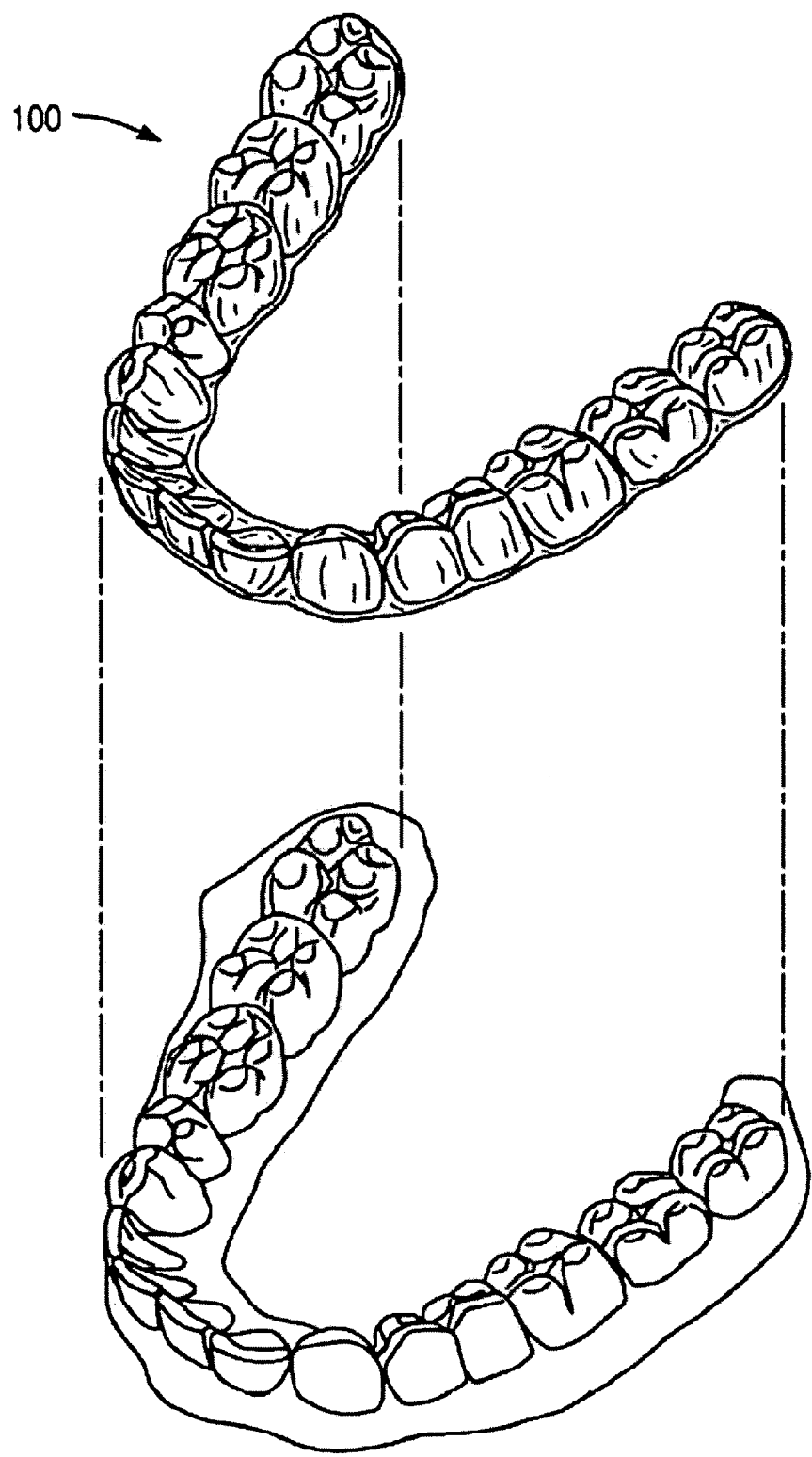
FIG. 1C illustrates the jaw of FIG. 1A together with an incremental position adjustment appliance which has been configured according to the methods of the present invention.

Referring now to FIG. 1C, systems according to the present invention will comprise a plurality of incremental position adjustment appliances. The appliances are intended to effect incremental repositioning of individual teeth in the jaw as described generally above. In a broadest sense, the methods of the present invention can employ any of the known positioners, retainers, or other removable appliances which are known for finishing and maintaining teeth positions in connection with conventional orthodontic treatment. The systems of the present invention, in contrast with prior apparatus and systems, will provide a plurality of such appliances intended to be worn by a patient successively in order to achieve the gradual tooth repositioning as described herein. A preferred appliance 100 will comprise a polymeric shell having a cavity shaped to receive and resiliently reposition teeth from one tooth arrangement to a successive tooth arrangement. The polymeric shell will preferably, but not necessarily, fit over all teeth present in the upper or lower jaw. Often, only certain one(s) of the teeth will be repositioned while others of the teeth will provide a base or anchor region for holding the repositioning appliance in place as it applies the resilient repositioning force against the tooth or teeth to be repositioned. In complex cases, however, many or most of the teeth will be repositioned at some point during the treatment. In such cases, the teeth which are moved can also serve as a base or anchor region for holding the repositioning appliance. Additionally, the gums and/or the palette can serve as an anchor region, thus allowing all or nearly all of the teeth to be repositioned simultaneously.

The polymeric appliance 100 of FIG. 1C is preferably formed from a thin sheet of a suitable elastomeric polymeric, such as Tru-Tain 0.03 in. thermal forming dental material, Tru-Tain Plastics, Rochester, Minn. 55902. Usually, no wires or other means will be provided for holding the appliance in place over the teeth. In some cases, however, it will be desirable or necessary to provide individual anchors on teeth with corresponding receptacles or apertures in the appliance 100 so that the appliance can apply an upward force on the tooth which would not be possible in the absence of such an anchor. Specific methods for producing the appliances 100 are described hereinafter.

Figure 2:
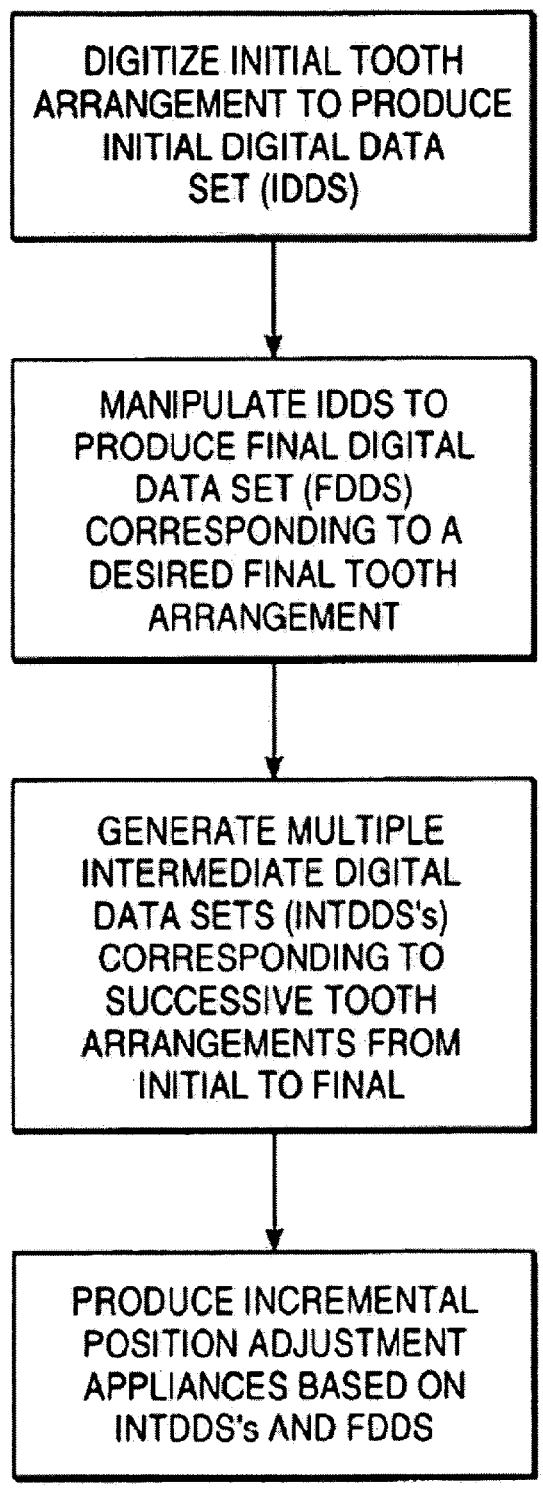
FIG. 2 is a block diagram illustrating the steps of the present invention for producing a system of incremental position adjustment appliances.

Referring now to FIG. 2, the overall method of the present invention for producing the incremental position adjustment appliances for subsequent use by a patient to reposition the patient's teeth will be described. As a first step, a digital data set representing an initial tooth arrangement is obtained, referred to hereinafter as the IDDS. The IDDS may be obtained in a variety of ways. For example, the patient's teeth may be scanned or imaged using well known technology, such as X-rays, three-dimensional X-rays, computer-aided tomographic images or data sets, magnetic resonance images, etc. Methods for digitizing such conventional images to produce data sets useful in the present invention are well known and described in the patent and medical literature. Usually, however, the present invention will rely on first obtaining a plaster cast of the patient's teeth by well known techniques, such as those described in Graber, *Orthodontics: Principle and Practice*, Second Edition, Saunders, Philadelphia, 1969, pp. 401-415. After the tooth casting is obtained, it can be digitally scanned using a conventional laser scanner or other range acquisition system to produce the IDDS. The data set produced by the range acquisition system may, of course, be converted to other formats to be compatible with the software which is used for manipulating images within the data set, as described in more detail below. General techniques for producing plaster casts of teeth and generating digital models using laser scanning techniques are described, for example, in U.S. Pat. No. 5,605,459, the full disclosure of which is incorporated herein by reference.

There are a variety of range acquisition systems, generally categorized by whether the process of acquisition requires contact with the three dimensional object. A contact-type range acquisition system utilizes a probe, having multiple degrees of translational and/or rotational freedom. By recording the physical displacement of the probe as it is drawn across the sample surface, a computer-readable representation of the sample object is made. A non-contact-type range acquisition device can be either a reflective-type or transmissive-type system. There are a variety of reflective systems in use. Some of these reflective systems utilize non-optical incident energy sources such as microwave radar or sonar. Others utilize optical energy. Those non-contact-type systems working by reflected optical energy further contain special instrumentation configured to permit certain measuring techniques to be performed (e.g., imaging radar, triangulation and interferometry).

A preferred range acquisition system is an optical, reflective, non-contact-type scanner. Non-contact-type scanners are preferred because they are inherently nondestructive (i.e., do not damage the sample object), are generally characterized by a higher capture resolution and scan a sample in a relatively short period of time. One such scanner is the Cyberware Model 15 manufactured by Cyberware, Inc., Monterey, Calif.

Either non-contact-type or contact-type scanners may also include a color camera, that when synchronized with the scanning capabilities, provides a means for capturing, in digital format, a color representation of the sample object. The importance of this further ability to capture not just the shape of the sample object but also its color is discussed below.

The methods of the present invention will rely on manipulating the IDDS at a computer or workstation having a suitable graphical user interface (GUI) and software appropriate for viewing and modifying the images. Specific aspects of the software will be described in detail hereinafter. While the methods will rely on computer manipulation of digital data, the systems of the present invention comprising multiple dental appliances having incrementally differing geometries may be produced by non-computer-aided techniques. For example, plaster casts obtained as described above may be cut using knives, saws, or other cutting tools in order to permit repositioning of individual teeth within the casting. The disconnected teeth may then be held in place by soft wax or other malleable material, and a plurality of intermediate tooth arrangements can then be prepared using such a modified plaster casting of the patient's teeth. The different arrangements can be used to prepare sets of multiple appliances, generally as described below, using pressure and vacuum molding techniques. While such manual creation of the appliance systems of the present invention will generally be much less preferred, systems so produced will come within the scope of the present invention.

Referring again to FIG. 2, after the IDDS has been obtained, the digital information will be introduced to the computer or other workstation for manipulation. In the preferred approach, individual teeth and other components will be "cut" to permit their individual repositioning or removal from the digital data. After thus "freeing" the components, the user will often follow a prescription or other written specification provided by the treating professional. Alternatively, the user may reposition them based on the visual appearance or using rules and algorithms programmed into the computer. Once the user is satisfied with the final arrangement, the final tooth arrangement is incorporated into a final digital data set (FDDS).

Based on both the IDDS and the FDDS, a plurality of intermediate digital data sets (INTDDS's) are generated to correspond to successive intermediate tooth arrangements. The system of incremental position adjustment appliances can then be fabricated based on the INTDDS's, as described in more detail below.

Figure 3:
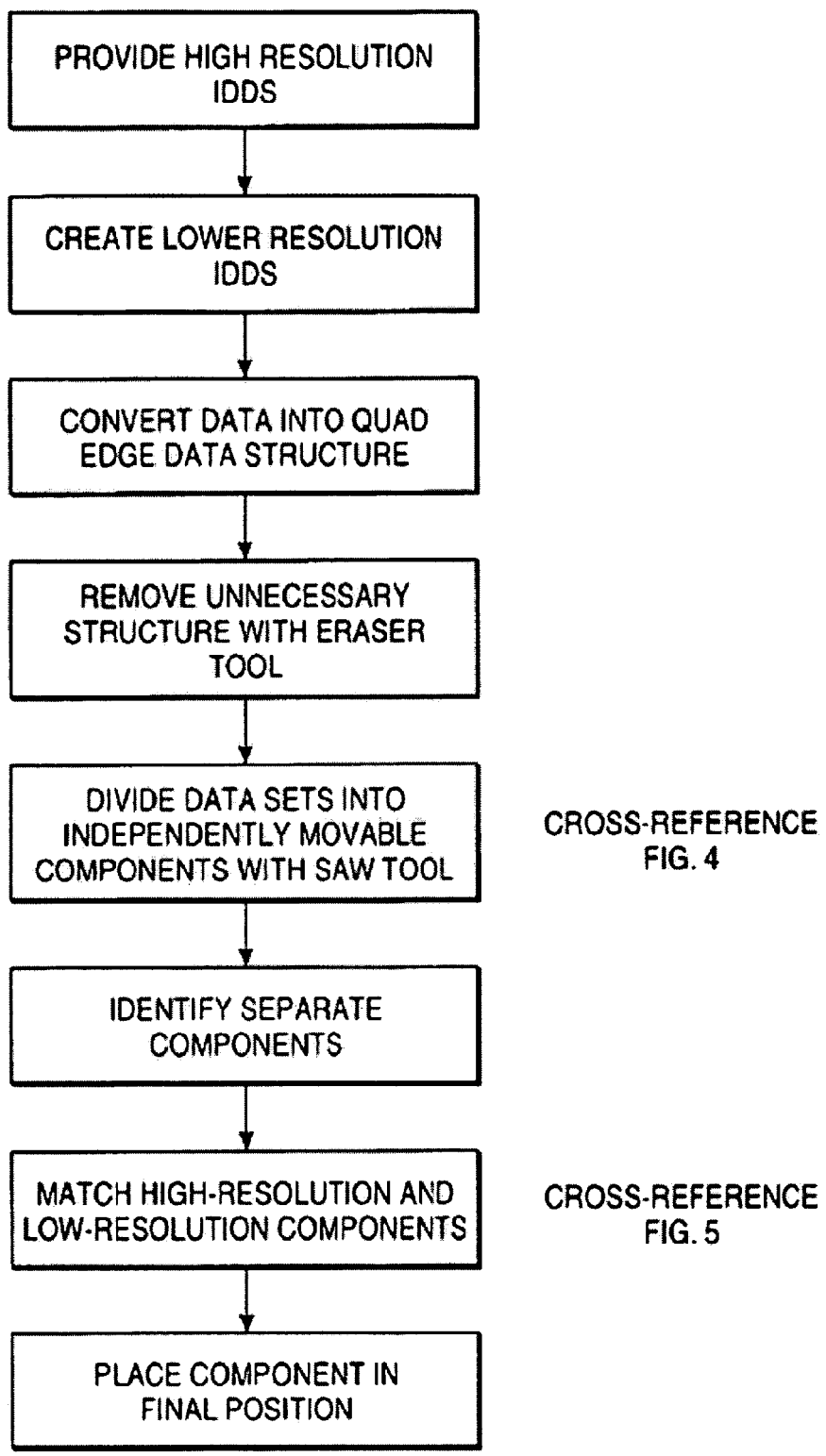
FIG. 3 is a block diagram setting forth the steps for manipulating an initial digital data set representing an initial tooth arrangement to produce a final digital data set corresponding to a desired final tooth arrangement.

FIG. 3 illustrates a representative technique for manipulating the IDDS to produce the FDDS on the computer. Usually, the data from the digital scanner will be in a high resolution form. In order to reduce the computer time necessary to generate images, a parallel set of digital data set representing the IDDS at a lower resolution will be created. The user will manipulate the lower resolution images while the computer will update the high resolution data set as necessary. The user can also view/manipulate the high resolution model if the extra detail provided in that model is useful. The IDDS will also be converted into a quad edge data structure if not already present in that form. A quad edge data structure is a standard topological data structure defined in *Primitives for the Manipulation of General Subdivisions and the Computation of Voronoi Diagrams*, ACM Transactions of Graphics, Vol. 4, No. 2, April 1985, pp. 74-123. Other topological data structures, such as the winged-edge data structure, could also be used.

As an initial step, while viewing the three-dimensional image of the patient's jaw, including the teeth, gingivae, and other oral tissue, the user will usually delete structure which is unnecessary for image manipulation and/or final production of an appliance. These unwanted sections of the model may be removed using an eraser tool to perform a solid modeling subtraction. The tool is represented by a graphic box. The volume to be erased (the dimensions, position, and orientation of the box) are set by the user employing the GUI. Typically, unwanted sections would include extraneous gum area and the base of the originally scanned cast. Another application for this tool is to stimulate the extraction of teeth and the "shaving down" of tooth surfaces. This is necessary when additional space is needed in the jaw for the final positioning of a tooth to be moved. The treating professional may choose to determine which teeth will be shaved and/or which teeth will be extracted. Shaving allows the patient to maintain their teeth when only a small amount of space is needed. Typically, extraction and shaving, of course, will be utilized in the treatment planning only when the actual patient teeth are to be extracted and/or shaved prior to initiating repositioning according to the methods of the present invention.

Removing unwanted and/or unnecessary sections of the model increases data processing speed and enhances the visual display. Unnecessary sections include those not needed for creation of the tooth repositioning appliance. The removal of these unwanted sections reduces the complexity and size of the digital data set, thus accelerating manipulations of the data set and other operations.

After the user positions and sizes the eraser tool and instructs the software to erase the unwanted section, all triangles within the box set by the user will be removed and the border triangles are modified to leave a smooth, linear border. The software deletes all of the triangles within the box and clips all triangles which cross the border of the box. This requires generating new vertices on the border of the box. The holes created in the model at the faces of the box are re-triangulated and closed using the newly created vertices.

The saw tool is used to define the individual teeth (or possibly groups of teeth) to be moved. The tool separates the scanned image into individual graphic components enabling the software to move the tooth or other component images independent of remaining portions of the model. The saw tool defines a path for cutting the graphic image by using two cubic B-spline curves lying in space, possibly constrained to parallel planes. A set of lines connects the two curves and shows the user the general cutting path. The user may edit the control points on the cubic B-splines, the thickness of the saw cut, and the number of erasers used, as described below.

Thickness: When a cut is used to separate a tooth, the user will usually want the cut to be as thin as possible. However, the user may want to make a thicker cut, for example, when shaving down surrounding teeth, as described above. Graphically, the cut appears as the curve bounded by half the thickness of the cut on each side of the curve.

Figure 4:
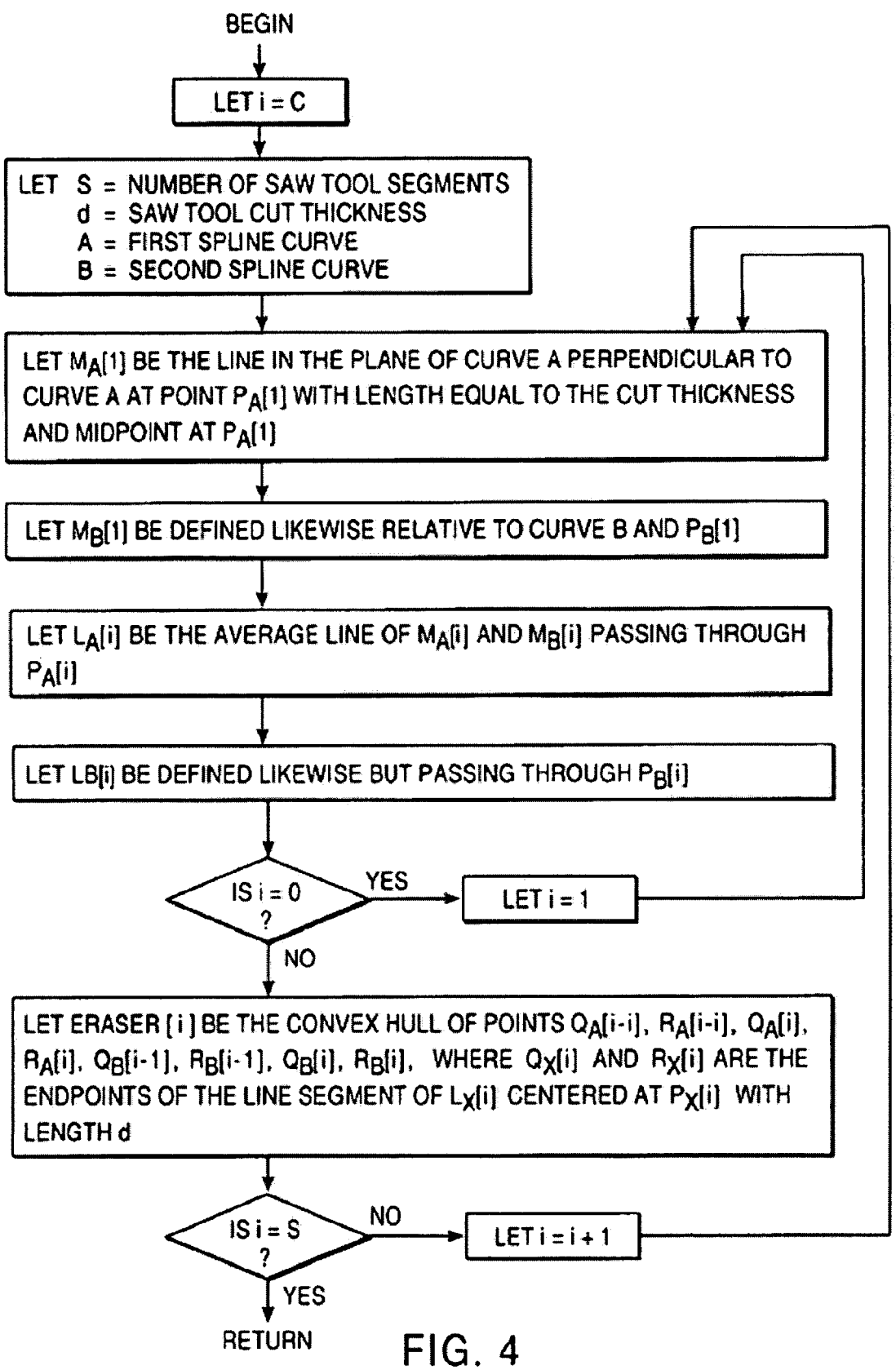
FIG. 4 is a flow chart illustrating an eraser tool for the methods herein.
Figure 4A:
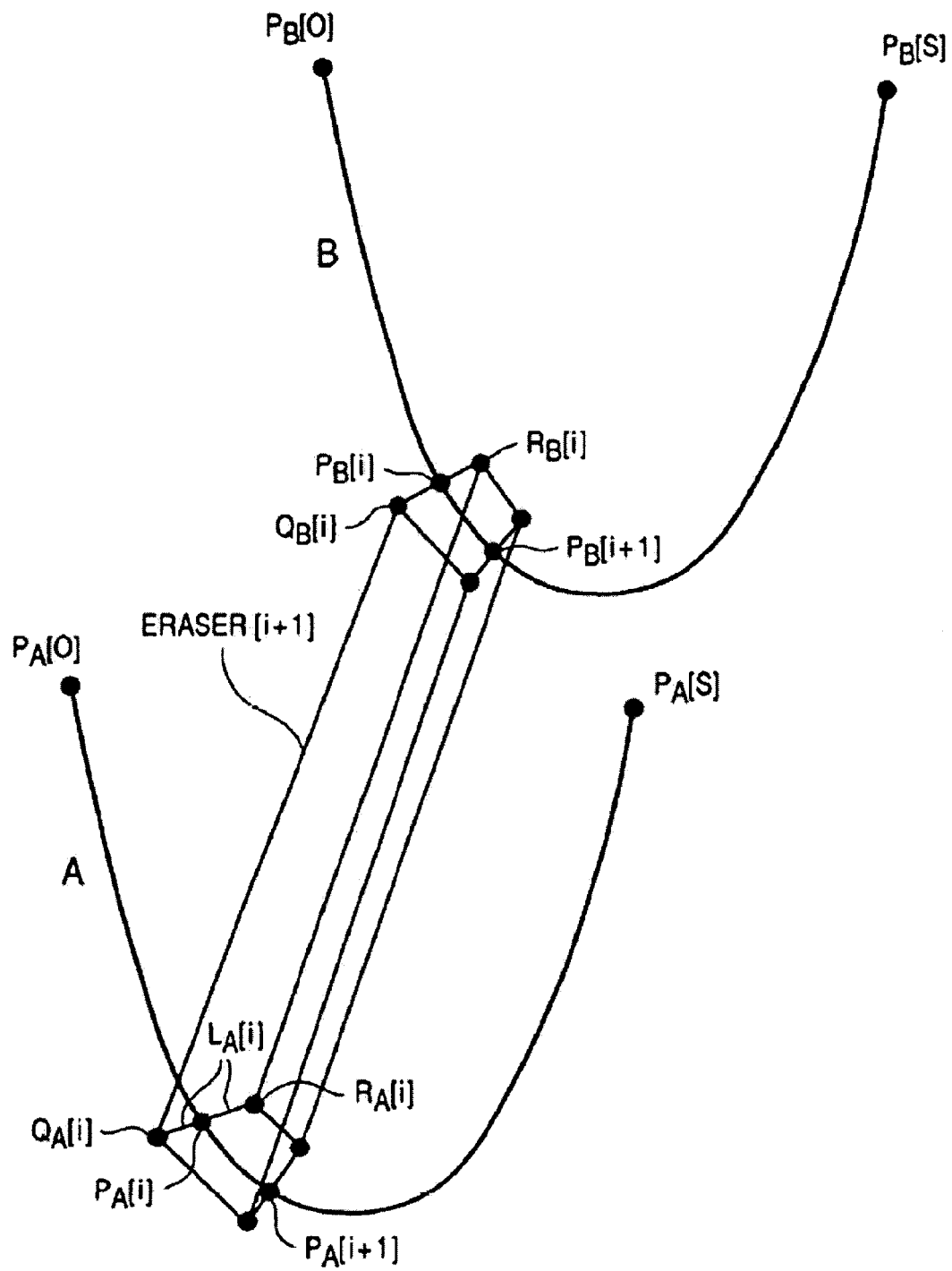
FIG. 4A illustrates the volume of space that is being erased by the program of FIG. 4.

Number of Erasers: A cut is comprised of multiple eraser boxes arranged next to each other as a piecewise linear approximation of the Saw Tool's curve path. The user chooses the number of erasers, which determines the sophistication of the curve created—the greater the number of segments, the more accurately the cutting will follow the curve. The number of erasers is shown graphically by the number of parallel lines connecting the two cubic B-spline curves. Once a saw cut has been completely specified the user applies the cut to the model. The cut is performed as a sequence of erasings. A preferred algorithm is set forth in FIG. 4. FIG. 4A shows a single erasing iteration of the cut as described in the algorithm.

A preview feature may also be provided in the software. The preview feature visually displays a saw cut as the two surfaces that represent opposed sides of the cut. This allows the user to consider the final cut before applying it to the model data set.

After the user has completed all desired cutting operations with the saw tool, multiple graphic solids exist. However, at this point, the software has not determined which triangles of the quad edge data structure belong to which components. The software chooses a random starting point in the data structure and traverses the data structure using adjacency information to find all of the triangles that are attached to each other, identifying an individual component. This process is repeated starting with the triangle whose component is not yet determined. Once the entire data structure is traversed, all components have been identified.

Figure 5:
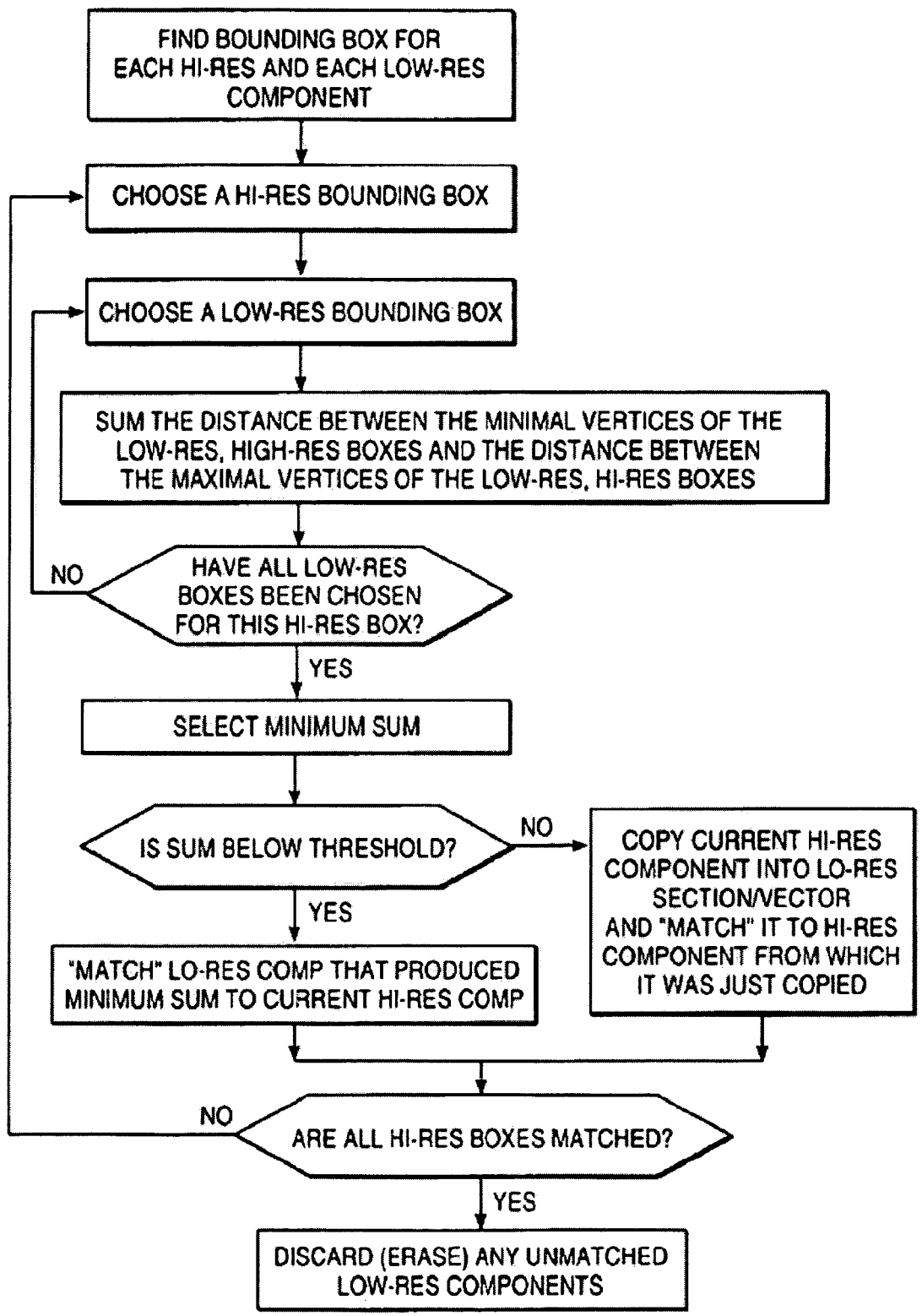
FIG. 5 is a flow chart illustrating a program for matching high-resolution and low-resolution components in the manipulation of data sets of FIG. 3.

To the user, all changes made to the high resolution model appear to occur simultaneously in the low resolution model, and vice versa. However, there is not a one-to-one correlation between the different resolution models. Therefore, the computer "matches" the high resolution and low resolution components as best as it can subject to defined limits. The algorithm is described in FIG. 5.

Figure 6:
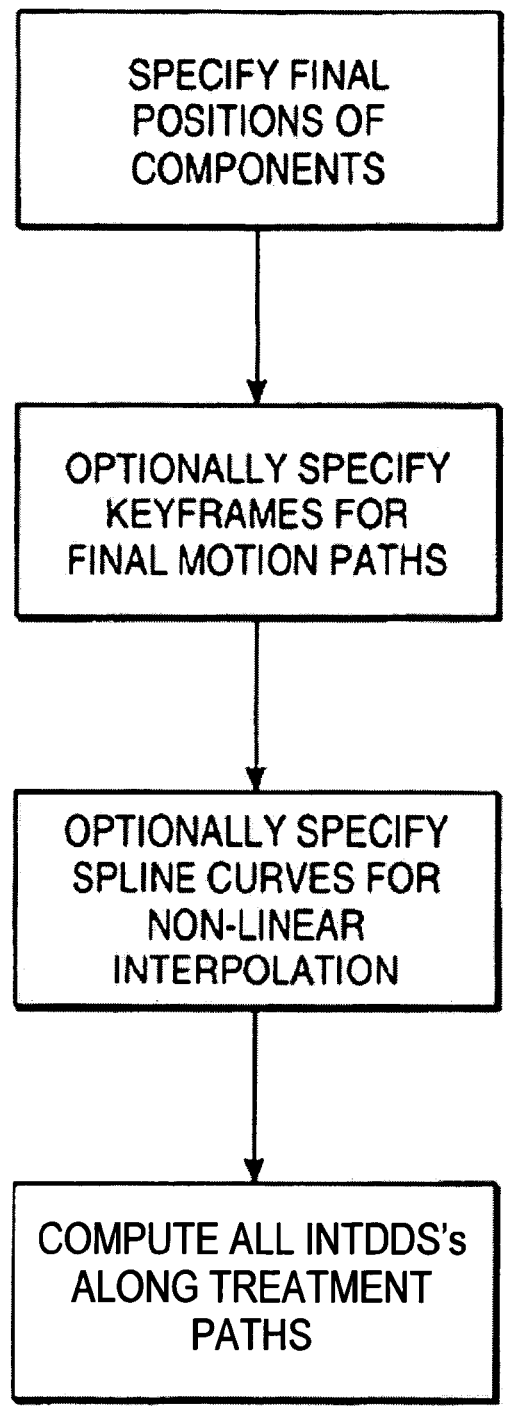
FIG. 6 illustrates the method for generating multiple intermediate digital data sets which are used for producing the adjustment appliances of the present invention.

After the teeth and other components have been placed or removed so that the final tooth arrangement has been produced, it is necessary to generate a treatment plan, as illustrated in FIG. 6. The treatment plan will ultimately produce the series of INTDDS's and FDDS as described previously. To produce these data sets, it is necessary to define or map the movement of selected individual teeth from the initial position to the final position over a series of successive steps. In addition, it may be necessary to add other features to the data sets in order to produce desired features in the treatment appliances. For example, it may be desirable to add wax patches to the image in order to define cavities or recesses for particular purposes. For example, it may be desirable to maintain a space between the appliance and particular regions of the teeth or jaw in order to reduce soreness of the gums, avoid periodontal problems, allow for a cap, and the like. Additionally, it will often be necessary to provide a receptacle or aperture intended to accommodate an anchor which is to be placed on a tooth in order to permit the tooth to be manipulated in a manner that requires the anchor, e.g., lifted relative to the jaw.

Some methods for manufacturing the tooth repositioning appliances require that the separate, repositioned teeth and other components be unified into a single continuous structure in order to permit manufacturing. In these instances, "wax patches" are used to attach otherwise disconnected components of the INTDDS's. These patches are added to the data set underneath the teeth and above the gum so that they do not effect the geometry of the tooth repositioning appliances. The application software provides for a variety of wax patches to be added to the model, including boxes and spheres with adjustable dimensions. The wax patches that are added are treated by the software as additional pieces of geometry, identical to all other geometries. Thus, the wax patches can be repositioned during the treatment path as well as the teeth and other components.

In the manufacturing process, which relies on generation of positive models to produce the repositioning appliance, adding a wax patch to the graphic model will generate a positive mold that has the same added wax patch geometry. Because the mold is a positive of the teeth and the appliance is a negative of the teeth, when the appliance is formed over the mold, the appliance will also form around the wax patch that has been added to the mold. When placed in the patient's mouth, the appliance will thus allow for a space between the inner cavity surface of the appliance and the patient's teeth or gums. Additionally, the wax patch may be used to form a recess or aperture within the appliance which engages an anchor placed on the teeth in order to move the tooth in directions which could not otherwise be accomplished.

In addition to such wax patches, an individual component, usually a tooth, can be scaled to a smaller or larger size which will result in a manufactured appliance having a tighter or looser fit, respectively.

Treatment planning is extremely flexible in defining the movement of teeth and other components. The user may change the number of treatment stages, as well as individually control the path and speed of components.

Number of Treatment Stages: The user can change the number of desired treatment stages from the initial to the target states of the teeth. Any component that is not moved is assumed to remain stationary, and thus its final position is assumed to be the same as the initial position (likewise for all intermediate positions, unless one or more key frames are defined for that component).

Key frames: The user may also specify "key frames" by selecting an intermediate state and making changes to component position(s). Unless instructed otherwise, the software automatically linearly interpolates between all user-specified positions (including the initial position, all key frame positions, and the target position). For example, if only a final position is defined for a particular component, each subsequent stage after the initial stage will simply show the component an equal linear distance and rotation (specified by a quatemion) closer to the final position. If the user specifies two key frames for that component, it will "move" linearly from the initial position through different stages to the position defined by the first key frame. It will then move, possibly in a different direction, linearly to the position defined by the second key frame. Finally, it will move, possibly in yet a different direction, linearly to the target position.

The user can also specify non-linear interpolation between the key frames. A spline curve is used to specify the interpolating function in a conventional manner.

These operations may be done independently to each component, so that a key frame for one component will not affect another component, unless the other component is also moved by the user in that key frame. One component may accelerate along a curve between stages 3 and 8, while another moves linearly from stage 1 to 5, and then changes direction suddenly and slows down along a linear path to stage 10. This flexibility allows a great deal of freedom in planning a patient's treatment.

Lastly, the software may incorporate and the user may at any point use a "movie" feature to automatically animate the movement from initial to target states. This is helpful for visualizing overall component movement throughout the treatment process.

Above it was described that the preferred user interface for component identification is a three dimensional interactive GUI. A three-dimensional GUI is also preferred for component manipulation. Such an interface provides the treating professional or user with instant and visual interaction with the digital model components. It is preferred over interfaces that permit only simple low-level commands for directing the computer to manipulate a particular segment. In other words, a GUI adapted for manipulation is preferred over an interface that accepts directives, for example, only of the sort: "translate this component by 0.1 mm to the right." Such low-level commands are useful for fine-tuning, but, if they were the sole interface, the processes of component manipulation would become a tiresome and time-consuming interaction.

Before or during the manipulation process, one or more tooth components may be augmented with template models of tooth roots. Manipulation of a tooth model augmented with a root template is useful, for example, in situations where impacting of teeth below the gumline is a concern. These template models could, for example, comprise a digitized representation of the patient's teeth x-rays.

The software also allows for adding annotations to the datasets which can comprise text and/or the sequence number of the apparatus. The annotation is added as recessed text (i.e. it is 3-D geometry), so that it will appear on the printed positive model. If the annotation can be placed on a part of the mouth that will be covered by a repositioning appliance, but is unimportant for the tooth motion, the annotation may appear on the delivered repositioning appliance(s).

The above-described component identification and component manipulation software is designed to operate at a sophistication commensurate with the operator's training level. For example, the component manipulation software can assist a computer operator, lacking orthodontic training, by providing feedback regarding permissible and forbidden manipulations of the teeth. On the other hand, an orthodontist, having greater skill in intraoral physiology and teeth-moving dynamics, can simply use the component identification and manipulation software as a tool and disable or otherwise ignore the advice.

Figure 7:
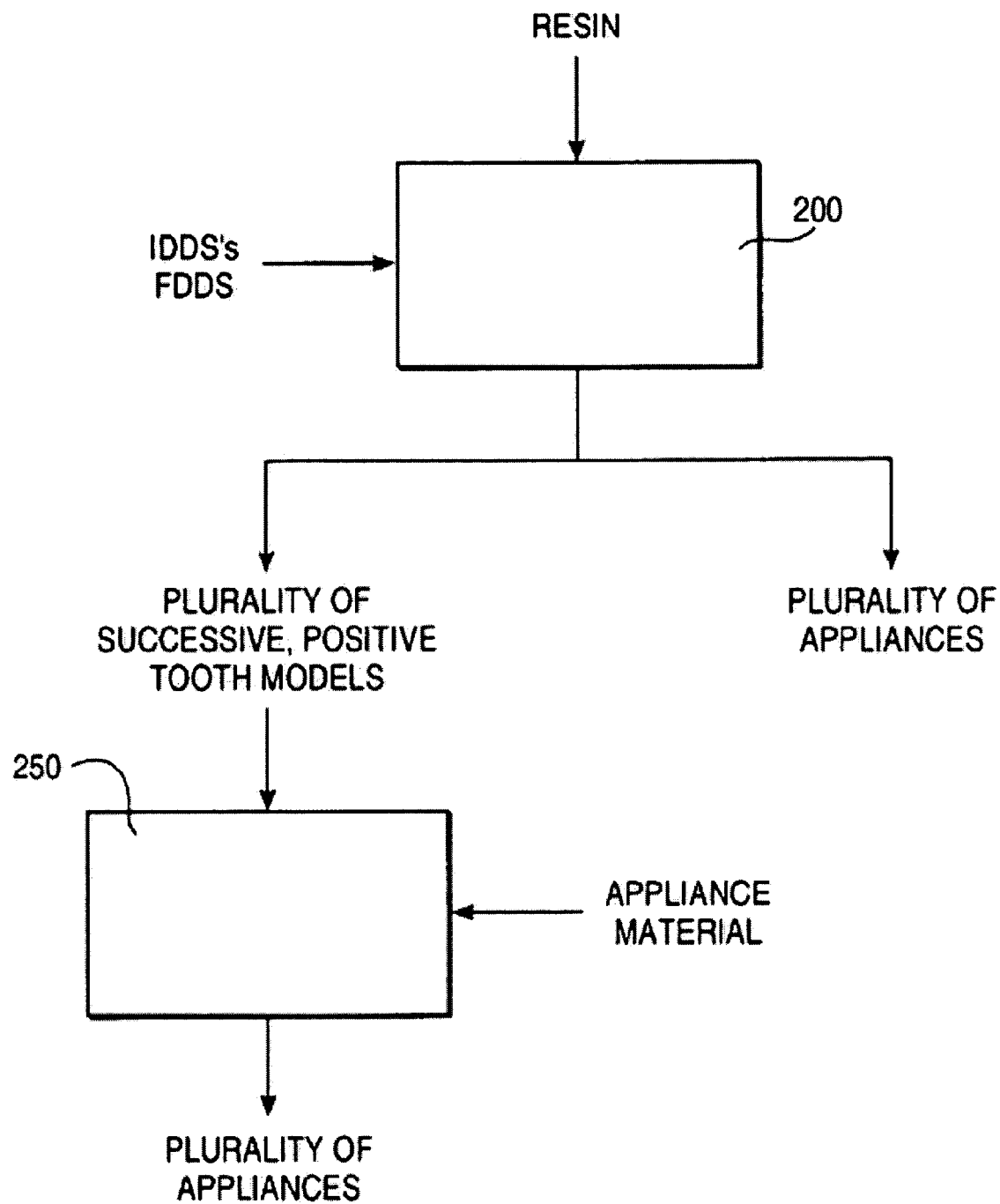
FIG. 7 illustrates alternative processes for producing a plurality of appliances according to the methods of the present invention utilizing digital data sets representing the intermediate and final appliance designs.

Once the intermediate and final data sets have been created, the appliances may be fabricated as illustrated in FIG. 7. Preferably, fabrication methods will employ a rapid prototyping device 200 such as a stereolithography machine. A particularly suitable rapid prototyping machine is Model SLA-250/50 available from 3D System, Valencia, Calif. The rapid prototyping machine 200 will selectively harden a liquid or other non-hardened resin into a three-dimensional structure which can be separated from the remaining non-hardened resin, washed, and used either directly as the appliance or indirectly as a mold for producing the appliance. The prototyping machine 200 will receive the individual digital data sets and produce one structure corresponding to each of the desired appliances. Generally, because the rapid prototyping machine 200 may utilize a resin having non-optimum mechanical properties and which may not be generally acceptable for patient use, it will be preferred to use the prototyping machine to produce molds which are, in effect, positive tooth models of each successive stage of the treatment. After the positive models are prepared, a conventional pressure or vacuum molding machine may be used to produce the appliances from a more suitable material, such as 0.03 inch thermal forming dental material, available from Tru-Tain Plastics, Rochester, Minn. 55902. Suitable pressure molding equipment is available under the trade name BIOSTAR from Great Lakes Orthodontics, Ltd., Tonawanda, N.Y. 14150. The molding machine 250 produces each of the appliances directly from the positive tooth model and the desired material. Suitable vacuum molding machines are available from Raintree Essix, Inc.

After production, the plurality of appliances which comprise the system of the present invention are preferably supplied to the treating professional all at one time. The appliances will be marked in some manner, typically by sequential numbering directly on the appliances or on tags, pouches, or other items which are affixed to or which enclose each appliance, to indicate their order of use. Optionally, written instructions may accompany the system which set forth that the patient is to wear the individual appliances in the order marked on the appliances or elsewhere in the packaging. Use of the appliances in such a manner will reposition the patient's teeth progressively toward the final tooth arrangement.

Figure 8:
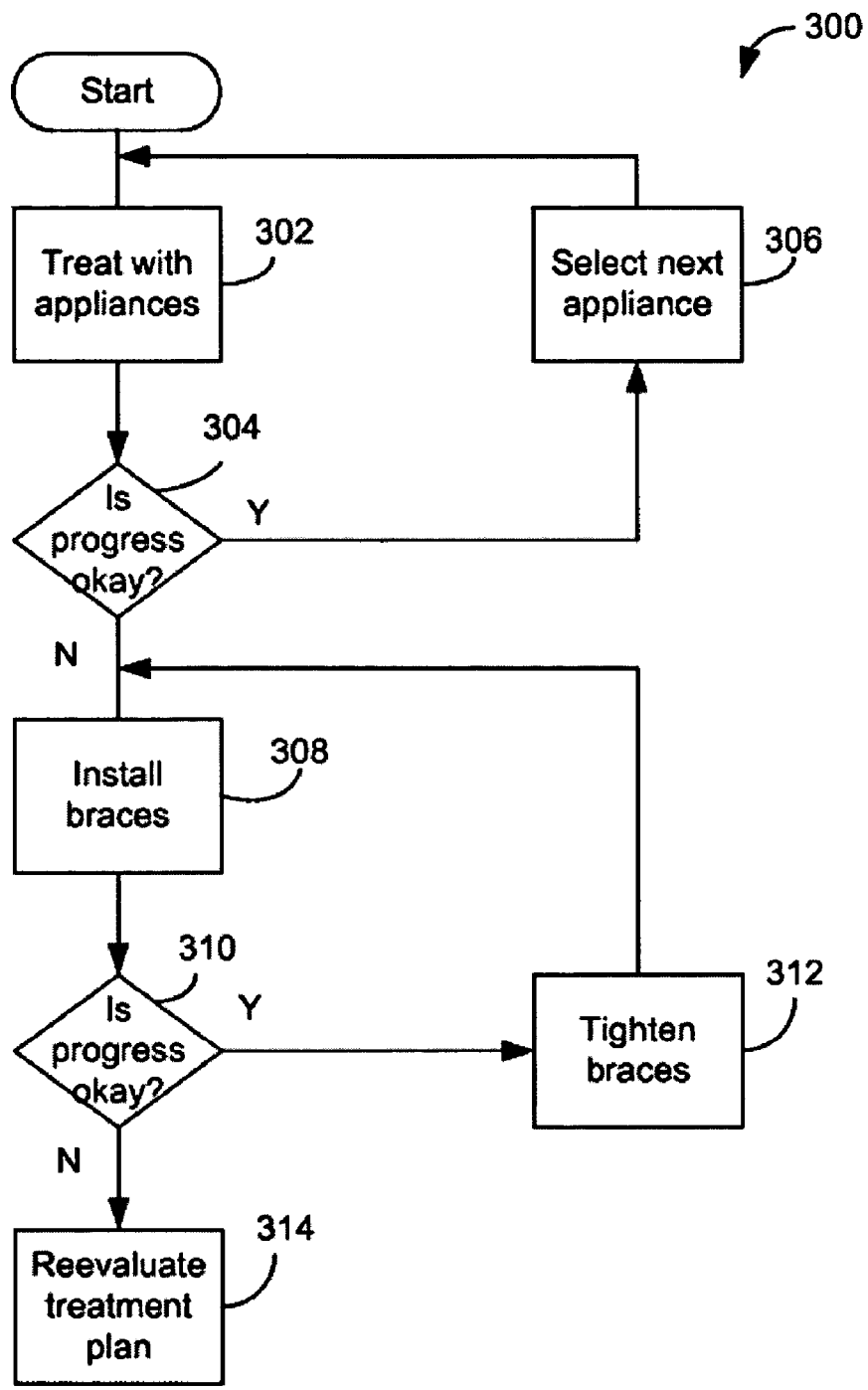
FIG. 8 is a flow chart illustrating one embodiment for treating teeth with appliances and braces.

FIG. 8 illustrates a process 300 relating to a hybrid treatment for complex cases where a combination of appliances and braces may be used. Before treatment, at least one appointment is typically scheduled with the orthodontist, dentist, and/or X-ray laboratory so that X-rays and photographs of the patient's teeth and jaw structure can be taken. Also during this preliminary meeting, or possibly at a later meeting, an alginate mold of the patient's teeth is typically made. This mold provides a model of the patient's teeth that the orthodontist uses in conjunction with the X-rays and photographs to formulate a treatment strategy and to produce appliances. The orthodontist then typically schedules one or more appointments during which appliances or braces can be attached to the patient's teeth.

In the embodiment of FIG. 8, the patient is treated with the appliances such as the appliance 100 of FIG. 1C (step 302). The patient may wear a series of appliances. For example, a treating professional such as an orthodontist may specify that the patient wear a new aligner every two weeks. Periodically, the progress of the treatment is evaluated by the patient's treating professional (step 304). If the patient is progressing according to plan with the appliances, the next appliance in the treatment sequence is provided to the patient and the process is repeated (step 306). If the patient's progress is unsatisfactory, the treating professional can consult with the patient to discuss treatment options, including a hybrid treatment solution where alternative teeth alignment devices are used in conjunction with the appliances to provide a complete treatment. The devices can be full or partial braces, properly timed serial extractions, headgear, functional appliances, or other removable appliances.

If a hybrid treatment option is selected, the process continues with step 308 wherein teeth straightening devices such as braces are installed. In one embodiment using braces, the treating professional reviews the patient's record, attaches brackets and mounts braces to the patient's teeth (step 308).

The braces may be removable or fixed (cemented and/or bonded to the teeth). They may be made of metal, ceramic or plastic. Molar bands are placed over the molar teeth and cemented into place. The molar bands usually have brackets welded or otherwise fixed thereon and these brackets provide an anchoring point for wires that pass through additional brackets cemented to the front teeth. The teeth surfaces are initially treated with a weak acid. The acid optimizes the adhesion properties of the teeth surfaces for brackets and bands that are to be bonded to them. The brackets and bands serve as anchors for other appliances to be added later. After the acid step, the brackets and bands are cemented to the patient's teeth using a suitable bonding material. No force-inducing appliances are added until the cement is set. For this reason, it is common for the orthodontist to schedule a later appointment to ensure that the brackets and bands are well bonded to the teeth. The primary force-inducing appliance in a conventional set of braces is the archwire. The archwire is resilient and is attached to the brackets by way of slots in the brackets. The archwire links the brackets together and exerts forces on them to move the teeth over time. Twisted wires or elastomeric O-rings are commonly used to reinforce attachment of the archwire to the brackets. Attachment of the archwire to the brackets is known in the art of orthodontia as "ligation" and wires used in this procedure are called "ligatures." The elastomeric O-rings are called "plastics."

Once the braces have been installed, the progress of the brace treatment process is periodically evaluated (step 310). Typically, these meetings are scheduled every three to six weeks. The treating professional periodically tightens the braces to place a constant, gentle force in a carefully controlled direction and to move teeth through their supporting bone to a new desirable position (312). The patient's braces may be adjusted by installing a different archwire having different force-inducing properties or by replacing or tightening existing ligatures. Alternatively, if the result of the evaluation at step 310 indicates that the treatment is unsatisfactory, then the treatment plan is reevaluated and the process of FIG. 8 can be repeated (step 314) until the teeth move to their intended destination.

Figure 9:
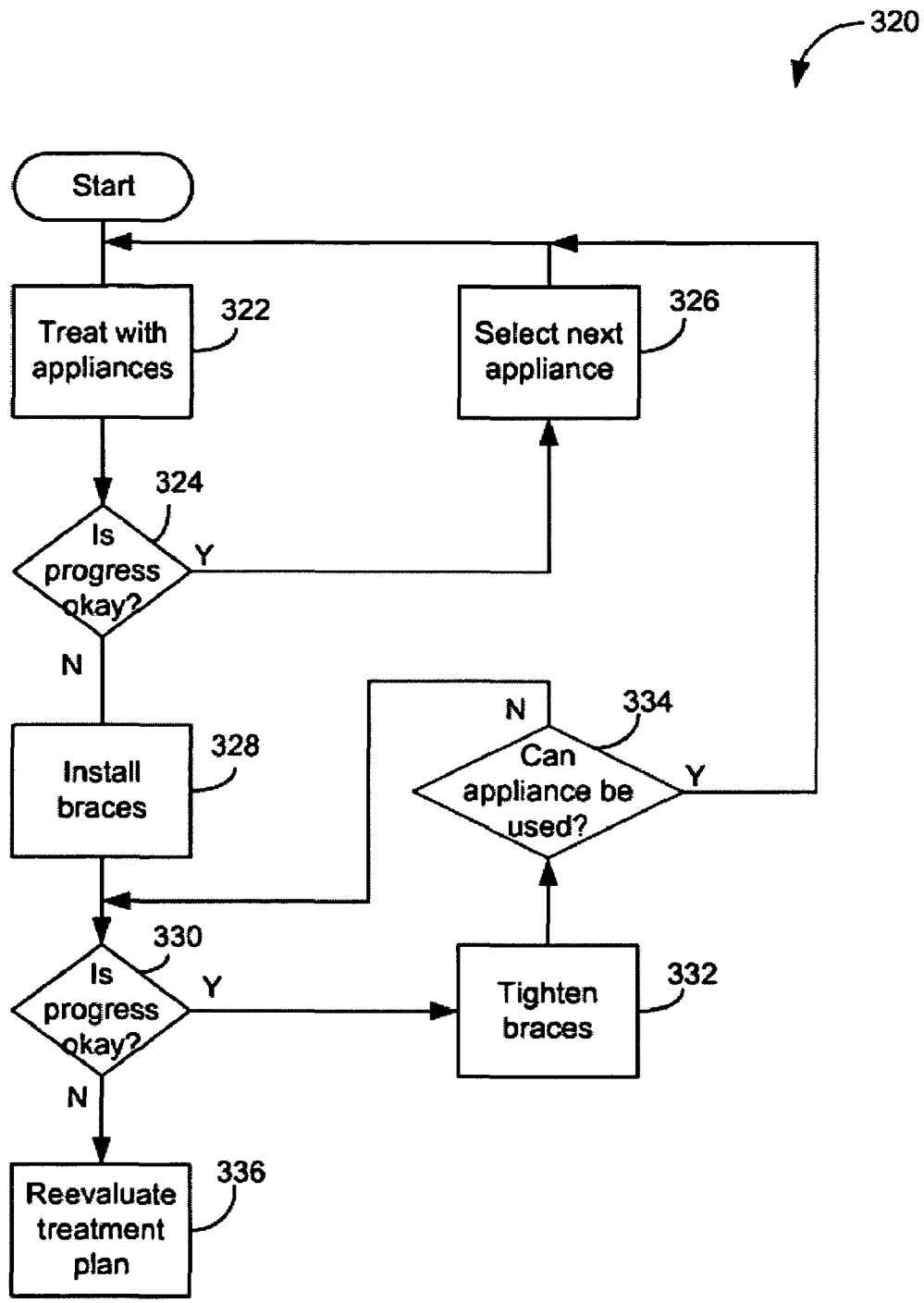
FIG. 9 is a flow chart illustrating a second embodiment for treating teeth with appliances and braces.

FIG. 9 shows a process 320 that is similar to the process of FIG. 8, but includes an option to use appliances after using the braces. Initially, the process 320 treats the teeth with appliances (step 322). The progress of the treatment is evaluated in step 324. If progress is made in a satisfactory manner in step 324, then the next appliance in the sequence is provided to the patient (step 326). If progress is unsatisfactory, then braces may be used. (step 328). Once the braces have been installed, progress is then again evaluated (step 330).

From step 330, if progress is unacceptable, then step 336 allows for a reevaluation of treatment plan.

If progress is satisfactory, then the braces may be tightened at step 332. An option then is to reevaluate the progress to see if an appliance can be used at step 334. If not, then the process continues back to step 330 to treat the patient with braces. Alternatively, if the appliance can be used, the process moves to step 322 to generate and deploy appliances for treatment.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for repositioning teeth from a first tooth arrangement to a subsequent tooth arrangement, the method comprising:

successively placing a plurality of appliances having cavities and wherein the cavities of successive appliances have different geometries selected to receive and progressively reposition the teeth from a first arrangement to successive arrangements, wherein treatment cavity geometries for at least two of the appliances are determined at the outset of treatment; and placing one or more wire and bracket systems to progressively reposition the teeth from a successive arrangement to a subsequent arrangement, the brackets being deployed in seriatim after successively placing appliances.

2. A method as in claim 1, further comprising determining a treatment plan at the outset of treatment.

3. A method as in claim 1, further comprising fabricating the appliances at the outset of treatment.

4. A method as in claim 1, further comprising replacing the appliances based on a predetermined schedule.

5. A method as in claim 1, further comprising reevaluating progress of repositioning of the teeth having wire and bracket systems to determine the need for subsequent appliances.

6. A method as in claim 5, further comprising placing one or more successive appliances having geometries selected to progressively reposition the teeth after the step of placing one or more wire and bracket systems.

7. A method as in claim 1, further comprising placing at least one attachment device on the teeth.

8. A method as in claim 7, wherein at least one appliance comprises an aperture formed in the appliance which corresponds to the attachment device.

9. A method as in claim 7, further comprising providing a multi-tooth attachment template for placing several attachment devices on the teeth.

10. A method for repositioning teeth from an initial tooth arrangement to a final tooth arrangement, the method comprising:

successively placing three or more appliances having cavities and wherein the cavities of successive appliances have different geometries selected to receive and progressively reposition the teeth from an initial arrangement to successive arrangements, wherein treatment cavity geometries for at least two of the appliances are determined prior to using any of the at least two appliances to progressively reposition the teeth; and placing one or more wire and bracket systems to progressively reposition the teeth from a successive arrangement to a final arrangement, the brackets being deployed in seriatim after successively placing appliances.

11. A method for repositioning teeth from a first tooth arrangement to a subsequent tooth arrangement, the method comprising:

successively placing a plurality of appliances having geometries selected to progressively reposition the teeth from a first arrangement to successive arrangements, wherein treatment cavity geometries for at least two of the appliances are determined prior to using any of the at least two appliances to progressively reposition the teeth;

placing one or more wire and bracket systems to progressively reposition the teeth from a successive arrangement to another arrangement, the brackets being deployed in seriatim after successively placing appliances; and subsequently placing one or more successive appliances having cavities and wherein the cavities of successive appliances have different geometries selected to receive and progressively reposition the teeth from the another arrangement to a subsequent arrangement.

12. A method for repositioning teeth from an initial tooth arrangement to a final tooth arrangement, the method comprising:

successively placing three or more appliances having cavities and wherein the cavities of successive appliances have different geometries selected to receive and progressively reposition the teeth from an initial arrangement to successive arrangements, wherein treatment cavity geometries for at least two of the appliances are determined prior to using any of the at least two appliances to progressively reposition the teeth;

placing one or more wire and bracket systems to progressively reposition the teeth from a successive arrangement to a subsequent arrangement, the brackets being deployed in seriatim after successively placing appliances; and subsequently placing one or more successive appliances having geometries selected to progressively reposition the teeth from the subsequent arrangement to a final arrangement.

13. A method for treating a dental malocclusion, the method comprising:

providing predetermined criteria for distinguishing a more severe malocclusion;

determining a treatment plan for an individual patient at the outset of treatment based on the criteria, wherein the treatment plan comprises:

placing one or more wire and bracket systems to progressively reposition the teeth from a first arrangement which is a more severe malocclusion to a successive arrangement which is a less severe malocclusion; and successively placing a plurality of appliances having cavities and wherein the cavities of successive appliances have different geometries selected to receive and progressively reposition the teeth from the successive arrangement to a subsequent arrangement, wherein treatment cavity geometries for at least two of the successive appliances are predetermined geometries which have been determined prior to using any of the at least two appliances to progressively reposition the teeth, the wire and bracket systems and appliances being deployed in seriatim to reposition teeth from the first arrangement to the subsequent arrangement.

14. A method as in claim 13, wherein the criteria characteristic of a more severe malocclusion includes at least some of the following:

A-P correction of greater than 2 mm;

autorotation of the mandible required for vertical/A-P correction;

CR-CO discrepancy correction/treatment to other than centric occlusion;

correction of moderate to severe rotations of premolars and/or cannines that are greater than 20 degrees;

severe deep bite opened to ideal or open bite to be closed to ideal;

extrusion of teeth greater than 1 mm other than as part of torquing or in conjunction with intrading adjacent teeth;

teeth tipped by more than 45 degrees;

multiple missing teeth;

crowns less than 70% of normal size;

posterior open bite; and movement of entire arch required for A-P correction.

15. A method as in claim 13, wherein the step of successively placing comprises placing at least two additional appliances having geometries selected to progressively reposition the teeth from the successive arrangement to the subsequent arrangement.

16. A method as in claim 13, wherein the step of successively placing comprises placing at least ten additional appliances having geometries selected to progressively reposition the teeth from the successive arrangement to the subsequent arrangement.

17. A method as in claim 13, wherein the appliances have been fabricated at the outset of treatment.

18. A method as in claim 13, further comprising replacing the appliances based on a predetermined schedule.

19. A method as in claim 13, further comprising placing at least one attachment device on the teeth.

20. A method as in claim 19, wherein at least one appliance comprises an aperture formed in the appliance which corresponds to the attachment device.

21. A method as in claim 19, further comprising providing a multi-tooth attachment template for placing several attachment devices on the teeth.

22. A method as in claim 13, wherein the more severe malocclusion comprises a malocclusion requiring treatment with a wire and bracket systems in order to achieve a desired reconfiguration of the teeth and a less severe malocclusion is a malocclusion that does not require treatment with a wire and bracket system in order to achieve a desired reconfiguration of the teeth.

23. A method for treating a dental malocclusion, the method comprising:

providing predetermined criteria for distinguishing a more severe malocclusion;

determining a treatment plan for an individual patient at the outset of treatment based on the criteria, wherein the treatment plan comprises:

placing one or more wire and bracket systems to progressively reposition the teeth from an initial arrangement which is a more severe malocclusion to a subsequent arrangement which is a less severe malocclusion; and successively placing three or more appliances having cavities and wherein the cavities of successive appliances have different geometries selected to receive and progressively reposition the teeth from the subsequent arrangement to a final arrangement, wherein treatment cavity geometries for at least two of the appliances are predetermined geometries which have been determined prior to using any of the at least two appliances to progressively reposition the teeth, the wire and bracket systems and appliances being deployed in seriatim to reposition teeth from the initial arrangement to the final arrangement.

24. A method for repositioning teeth from an initial tooth arrangement to a final tooth arrangement, the method comprising:

placing an attachment template over several teeth;

placing several attachment devices to the teeth with the template;

successively placing a plurality of appliances having cavities and wherein the cavities of successive appliances have different geometries selected to receive and progressively reposition the teeth form a first arrangement to successive arrangements, wherein treatment cavity geometries for at least two of the appliances are determined prior to using any of the at least appliances to progressively reposition the teeth; and placing one or more wire and bracket systems to progressively reposition the teeth from one arrangement to a successive arrangement, the brackets and appliances being deployed in seriatim to reposition teeth from the initial tooth arrangement to the final tooth arrangement.

25. A method as in claim 24, wherein the attachment template comprises an appliance.

26. A method as in claim 24, wherein the attachment template comprises a handle.

27. A method as in claim 24, wherein the attachment template comprises at least one negative impression of an attachment device.

28. A method as in claim 24, wherein at least one appliance has an aperture formed in the appliance which corresponds to the attachment device.

29. A method as in claim 24, further comprising determining a treatment plan at the outset of treatment.

30. A method as in claim 24, further comprising fabricating the appliances at the outset of treatment.

31. A method as in claim 24, further comprising replacing the appliances based on a predetermined schedule.

32. A method as in claim 24, further comprising determining positions of the attachment devices prior to treatment.

33. A method for repositioning teeth from a first tooth arrangement to a subsequent tooth arrangement, the method comprising:

successively placing a plurality of appliances having cavities and wherein the cavities of successive appliances have different geometries selected to receive and progressively reposition the teeth from a first arrangement to successive arrangements, wherein treatment cavity geometries for at least two of the appliances are determined prior to using any of the at least two appliances to progressively reposition the teeth; and placing one or more wire and bracket systems to progressively reposition the teeth from a successive arrangement to a subsequent arrangement, the appliances and wire and bracket systems being deployed in seriatim to reposition teeth from the first arrangement to the subsequent arrangement.

* * * * *